(12) United States Patent
Yang et al.

(10) Patent No.: US 7,008,633 B2
(45) Date of Patent: Mar. 7, 2006

(54) LOCAL REGIONAL CHEMOTHERAPY AND RADIOTHERAPY USING IN SITU HYDROGEL

(75) Inventors: David J. Yang, Sugar Land, TX (US); Dong-Fang Yu, Houston, TX (US); Ali Azhdarinia, Houston, TX (US); Tommy L. Lee, Spring, TX (US); E. Edmund Kim, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 254 days.

(21) Appl. No.: 10/024,678

(22) Filed: Dec. 18, 2001

(65) Prior Publication Data

US 2005/0227910 A1    Oct. 13, 2005

Related U.S. Application Data

(60) Provisional application No. 60/256,514, filed on Dec. 18, 2000.

(51) Int. Cl.
   *A61F 13/00*    (2006.01)
   *A61K 9/14*     (2006.01)
   *A61K 48/00*    (2006.01)

(52) U.S. Cl. ............... 424/422; 424/484; 424/488; 424/93.21

(58) Field of Classification Search ............... 424/422, 424/484, 488, 93.21; 604/82
   See application file for complete search history.

(56) References Cited

U.S. PATENT DOCUMENTS

| | | | |
|---|---|---|---|
| 4,587,268 A | 5/1986 | Pfirrmann | |
| 5,257,970 A | 11/1993 | Dougherty | |
| 5,470,843 A | 11/1995 | Stahl et al. | |
| 5,542,935 A | 8/1996 | Unger et al. | |
| 5,571,797 A | 11/1996 | Ohno et al. | |
| 5,656,272 A | 8/1997 | Le et al. | |
| 5,702,717 A | 12/1997 | Cha et al. | |
| 5,945,100 A | * 8/1999 | Fick | 424/93.21 |
| 5,977,163 A | 11/1999 | Li et al. | |
| 5,989,215 A | * 11/1999 | Delmotte et al. | 604/82 |
| 6,004,573 A | 12/1999 | Rathi et al. | |
| 6,117,949 A | 9/2000 | Rathi et al. | |

FOREIGN PATENT DOCUMENTS

JP    10236984 A2    9/1993

(Continued)

OTHER PUBLICATIONS

Burris III, Howard A., et al.; Intratumoral cisplatin/epinephrine-injectable gel as a palliative treatment for accessible solid tumors: A multicenter pilot center; Head Neck Surg; vol. 118; pp. 496-503; 1998.

(Continued)

*Primary Examiner*—Thurman K. Page
*Assistant Examiner*—Blessing Fubara
(74) *Attorney, Agent, or Firm*—Fulbright & Jaworski, LLP

(57) ABSTRACT

Methods regarding local regional treatment in situ for an individual, such as of a tumor, are provided herein. A hydrogel composition is generated in situ in the tumor by administering a polymer, such as a polysaccharide or a polyamino acid, with a therapeutic agent, such as a radionuclide or a drug, and administering a cross-linking agent. The hydrogel/therapeutic agent composition is retained in the tumor for safe and efficient tumor therapy. Alternatively, a hydrogel composition is generated in situ in an artery which nourishes a tumor to occlude the artery.

61 Claims, 9 Drawing Sheets

FOREIGN PATENT DOCUMENTS

| | | |
|---|---|---|
| JP | 7097401 A2 | 4/1995 |
| WO | WO-00/00222 | 1/2000 |
| WO | WO-00/38651 | 7/2000 |

OTHER PUBLICATIONS

Downs, Elizabeth C., et al.; Calcium Alginate Beads as a Slow-Release System for Delivering Angiogenic Molecules In Vivo and In Vitro; Journal of Cellular Physiology; vol. 152; pp. 422-429; 1991.

Smith, Jill P., et al.; Drug retention and distribution after intratumoral chemotherapy with fluorouracil/epinephrine injectable gel in human pancreatic cancer xenografts; Cancer Themother Pharmacol; vol. 44; pp. 267-274; 1999.

Ning, Shoucheng, et al.; Radiosensitization by intratumoral administration of cisplatin in a sustained-release drug delivery system; Radiotherapy and Oncology; vol. 50; pp. 215-223; 1999.

Monga, Satdarshan P.S., et al.; Intratumoral Therapy of Cisplatin/Epinephrine Injectable Gel for Palliation in Patients With Obstructive Esophageal Cancer; Am J. Clin. Oncol.; vol. 23(4); pp. 386-392; 2000.

Miller, Bruce H., et al.; Nonsurgical treatment of basal cell carcinomas with intralesional 5-fluorouracil/epinephrine injectable gel; Journal of the American Academy of Dermatology; vol. 36 (1); pp. 72-77; 1977.

Jackson, John K., et al.; The Suppression of Human Prostate Tumor Growth in Mice by the Intratumoral Injection of a Slow-Release Polymeric Paste Formulation of Paclitaxel; Cancer Research; vol. 60; pp. 4146-4151; 2000.

SPECT abnormalities in Landau-Kleffner syndrome; Journal of Clinical Neuroscience; vol. 6 (1); pp. 9-16; 1999.

Kitazawa, Hidenori, et al.; Microdialysis Assessment of Fibrin Glue Containing Sodium Alginate for Local Delivery of Doxorubicinin Tumor-Bearing Rats; Biol. Pharm. Bull.; vol. 20.

Kraus, Jurgen, et al.; Alternative promoter usage and tissue specific expression of the mouse somatostatin receptor 2 gene; Federation of European Biochemical Societies Letters; vol. 428; pp. 165-170; 1998.

Kuang, Liren, et al.; Percutaneous intratumoral injectino of cisplatin microspheres in tumor-bearing rats to diminish acute nephrotoxicity; Anti-Cancer Drugs; vol. 7; pp. 220-227; 1996.

* cited by examiner

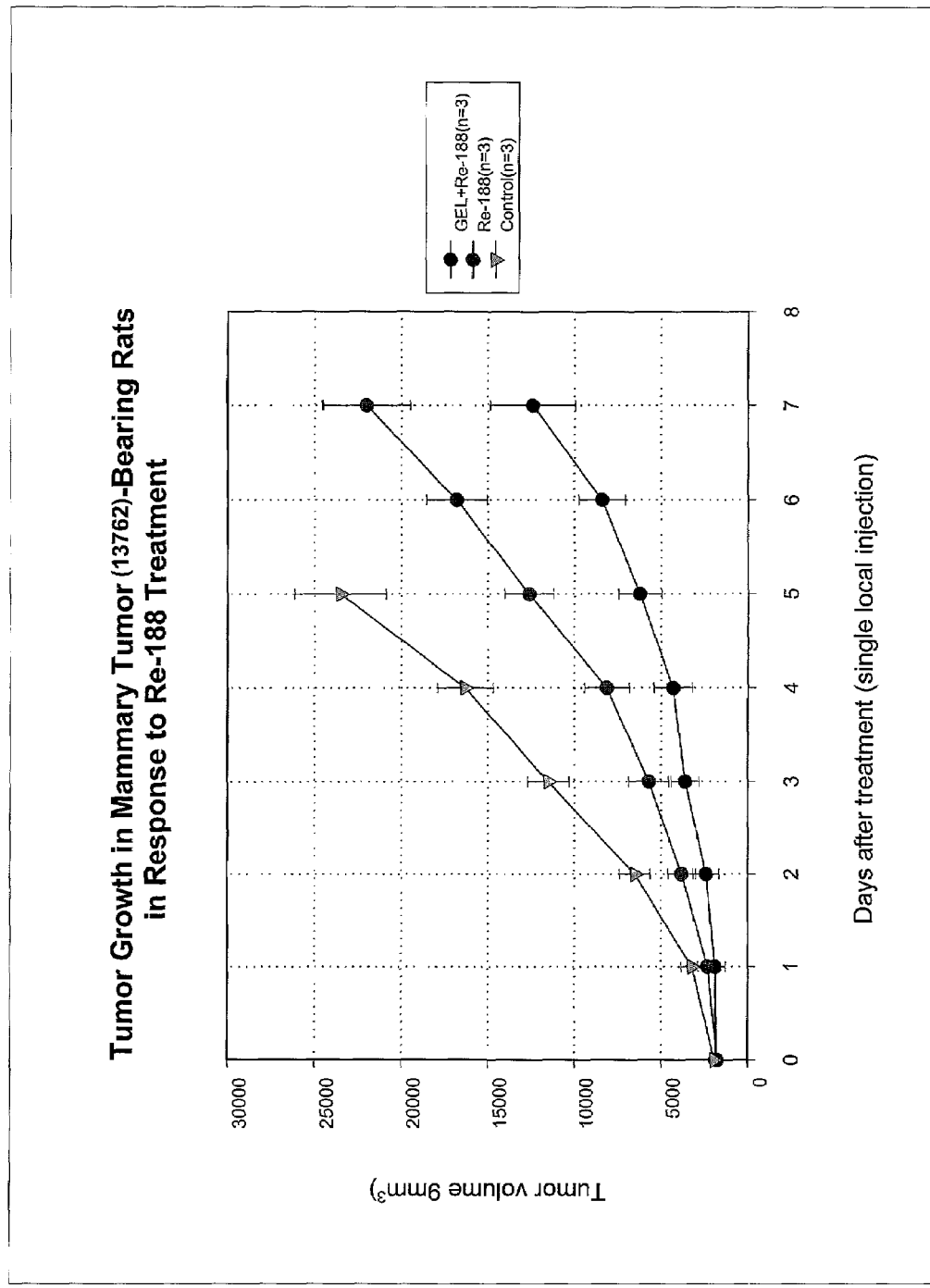

LOCAL REGIONAL CHEMOTHERAPY AND RADIOTHERAPY USING IN SITU HYDROGEL

This application claims priority to U.S. Provisional Patent Application Ser. No. 60/256,514 filed Dec. 18, 2000.

BACKGROUND OF THE INVENTION

1. Field of the Invention

The present invention is directed to the fields of disease therapy, cancer biology, and cancer therapy. More specifically, the present invention is directed to providing local regional treatment in an individual in situ by administering a polymer and a cross-linking agent. More preferably, the local regional treatment in situ is of a tumor in the individual.

2. Description of Related Art

Systemic administration of anticancer agents often results in severe dose-limiting toxic effects. Therefore, site-specific delivery of anticancer drugs, such as in local regional therapy, is extremely beneficial for solid tumors. During local regional therapy for treatments of tumors, current methods include transcatheter arterial chemoembolization (TACE), brachytherapy, and peritumor/intralesional injection. Patients with malignancies which are inoperable or unsuitable for surgery often have a poor prognosis, and current palliative treatments have an associated morbidity and mortality.

Primary and metastatic tumors may receive their blood supply predominantly or entirely from the arteries. TACE with various kinds of anticancer drugs has been considered an effective method of treating unresectable primary tumors and metastases. The potential therapeutic effect results from the combination of embolic occlusion of the blood supply to the neoplasms and local retention of the infused chemotherapeutic drugs. Agents currently used to achieve vascular occlusion include, for example, lipiodol (iodized oil). However, conventional TACE has some disadvantages. Specifically, materials currently used for chemoembiolization, i.e., particles and lipid, occlude tumor vessels incompletely. Intraorgan collateral vessels rapidly develop around the occlusions, and effective dearterialization of the organ may be difficult to achieve even after repeated embolization. For example, it is known that shortly after hepatic vessels were embolized with Gelfoam powder, portions of the intrahepatic arteries in various parts of the liver were reconstituted via microcollaterals. Although lipiodal chemoembolization has been considered the most effective of these methods, on the basis of reports of a decrease in tumor size in a nonrandomized trial, the embolization effect is questionable. One study suggested that lipiodal has no thromboembolic effect. There was no statistically significant difference in tissue necrosis in lipiodol-injected hepatocellular carcinoma versus noninjected controls. Repeated peripheral embolization of the hepatic artery with very small particles can cause occlusion of the collateral vessels as well as the primary hepatic artery, but this might well result in necrosis of normal tissue as well as tumor in patients whose metastases are being embolized. In addition, complications are frequent and side effects have been reported.

Tumor vascularity has been identified as a prominent prognostic factor for patients receiving regional chemotherapy of tumors given that multiple prognostic factors for survival are related both to growth of the tumor. Presumably, particles and lipid drops cause discontinuous embolization of tumor vessels, since unoccluded microcirculation of collateral vessels may continue to supply the tumor cells. Therefore, to overcome the problem of conventional TACE, a better strategy to improve cancer therapy by TACE should include complete occlusion of tumor vessels, damaging normal tissue as little as possible, and preventing the formation of collaterals.

Tumor therapy also includes utilization of irradiation of a tumor for eradication purposes. Brachytherapy methods utilize small particles or seeds of radioactivity implanted into a tumor and are used often in cervical, breast, endometrial, prostate, and head and neck cancers. However, current brachytherapy seed-dispensing methods dictate less than desirable loading yields, are more expensive, are cumbersome to administer, and render a less than ideal treatment response.

In another technology requiring surgical intervention, patients with operable brain tumors, such as glioblastoma multiforme, are subjected to tumor removal through surgical means, and GLIADEL® (Nova Pharmaceutical Corporation; Baltimore, Md.) biodegradable wafers made of a polyanhydride, such as polifeprosan 20, containing a chemotherapeutic are inserted into the remaining cavity. However, this method requires surgical removal of the tumor, which is not always feasible.

Peritumor/intralesional injection is another method in the art for administering a chemotherapeutic drug to a tumor. Numerous examples exist in the art wherein a chemotherapeutic is administered intratumorally in a gel as a sustained-release delivery system, such as an epinephrine (epi) gel (Miller et al., 1997; Burris et al., 1998; Kraus et al., 1998; Harbord et al., 1999; Ning et al., 1999; Smith et al., 1999; Monga et al., 2000). Alternatively, polymers are utilized as slow-release matrices including, for instance, a blend of copolymers (Jackson et al., 2000). However, these sustained release delivery systems administered by direct injection are subject to leakage into surrounding tissues in the absence of an agent, such as a cross-linking agent, or other means to retain the chemotherapeutic within the tumor itself.

Chinese Patent No. 1252310 is directed to a preparation having a medicine powder with a gel and cross-linked by, for example, calcium for local injection treatment and artery embolism treatment. However, the preparation is generated outside the body and not in situ in the tumor. Similarly, although Japanese Patent No. 10236984 regards a fibrin-containing composition for sustained release of a medical component and Japanese Patent No. 7097401 is directed to a bridged hyaluronic acid as a sustained-release preparation or an embolizing agent, neither patent concerns generation of the medicinal component/preparations within a tumor. Furthermore, none of the methods or polymer compositions in these patents utilize radionuclides as therapeutic agents.

U.S. Pat. No. 5,257,970 regards encapsulation of a drug in a liposome, injection of a photosensitizer into a host, injection of the liposome-encapsulated preparation systemically, and heating of a tumor to melt the liposome to allow mixing of the activation components.

Downs et al. (1992) use calcium alginate beads as a slow-release system of administering growth factors. However, the growth factor/sodium alginate compositions were created and uniform beads were obtained ex vivo by passing the mixture of beads through a syringe. This process is cumbersome and generates significant loss of therapeutic material, which can be costly.

Kitazawa et al. (1997) utilize a fibrin glue as a drug carrier for the chemotherapeutic doxorubicin and determine there is an improvement in sustained release in the presence of sodium alginate. Again, the fibrin (fibrinogen) sodium alginate powder was generated outside of the body of the tumor-bearing rats.

PCT Application WO 00/00222 is directed to sustained release of pharmaceutical compositions with a thermosensitive, biodegradable hydrogel consisting of a block copolymer of poly(d,1-1-lactic acid) or poly(lactide-co-glycolide) and polyethylene glycol. The polymerix matrix containing the pharmaceutical concentration is injected into the tumor to create a gel in vivo. However, the gel formation is temperature-activated and generates only after sufficient time to reach the required temperature, thereby permitting leakage into surrounding tissues in the meantime. PCT Application WO 00/38651 concerns a similar technology further comprising pH-responsive gelation/degelation properties.

U.S. Pat. Nos. 6,004,573; 6,117,949; and 5,702,717 are directed to a injectable biodegradable polymeric liquid matrix containing a drug which becomes a gelatinous composition after it reaches body temperature.

Thus, the absence in the art of a method to administer in situ an anticancer drug with high loading yields for a drug carrier, absence of leakage into surrounding tissues, lower cost, ease of process and better treatment response is fulfilled with the methods of the present invention.

SUMMARY OF THE INVENTION

In an embodiment of the present invention, there is a method of dispensing a therapeutic agent in situ to a localized region in an individual comprising administering to said region a polymer composition that comprises a biocompatible polymer, a cross-linking composition that comprises a cross-linker, and the therapeutic agent, wherein the polymer composition and the cross-linking composition are administered to allow formation of a cross-linked polymer in situ at the localized region, which cross-linked polymer comprises the therapeutic agent. In a specific embodiment, the polymer composition comprises the therapeutic agent.

In another specific embodiment, the polymer composition and the cross-linking composition are separately administered to the localized region. In an additional specific embodiment, the polymer composition and the cross-linking composition are administered to the localized region from separate containers, wherein a first container contains the polymer composition and a second container comprises the cross-linking composition. In another specific embodiment, the first and second containers are syringes. In an additional specific embodiment, the polymer composition and the cross-linking composition are administered to said region by means of a single container having at least two compartments, wherein one compartment comprises the polymer composition and another compartment comprises the cross-linking composition. In an additional specific embodiment, the polymer composition and the cross-linking composition are administered to the region by means of a single container having a hollow cylindrical compartment, wherein the polymer composition and cross-linking composition are administered separately through said compartment. In another specific embodiment, the separate administrations of said polymer composition and said cross-linking composition are by syringe. In an additional specific embodiment, the polymer composition and cross-linking compositions are administered separately from a syringe having at least two compartments.

In an additional specific embodiment, the polymer is a polysaccharide, a polyamino acid polymer, or a combination thereof. In an additional specific embodiment, the polymer is a polysaccharide, and the polysaccharide polymer is an alginate, hydroxycellulose, chondroitin, chitosan, hyaluronate, dextran, or starch. In another specific embodiment, the polymer is a polyamino acid, and the polyamino acid is a polyglutamate or a polyaspartate. In another specific embodiment, the cross-linking agent is a salt of a divalent cation. In another specific embodiment, divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{2+}$. In another specific embodiment, the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, F manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide.

In an additional specific embodiment, the therapeutic agent is a drug, a hormone, a gene therapy composition, a radionuclide, a nutriceutical, or a combination thereof. In another specific embodiment, the therapeutic agent is a drug, and the drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, penicillin, erythromycin, amoxicillin, cefazolin, imipenem, aztreonam, sulbactam, linezolid, gentamicin, sulfamethoxazole, vancomycin, ciprofloxacin, fusidic acid, trimethoprim, metronidazole, clindamycin, mupirocin, amphotericin B, rifampin, fluconazoleor, or a combination thereof. In an additional specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2a}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof.

In another specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-1, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, or a combination thereof. In an additional specific embodiment, the vector is a plasmid, an adenoviral vector, an adeno-associated viral vector, a retroviral vector, a liposome, or a combination thereof. In an additional specific embodiment, the therapeutic agent is a radionuclide, and the radionuclide is $^{188}$Re, $^{213}$Bi, $^{166}$Ho, $^{211}$At, or a combination thereof. In another specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gynmema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In another specific embodiment, the therapeutic agent further comprises a detectable identifier, wherein the detectable identifier is an X-ray contrasting agent, a CT contrasting agent, an MRI contrasting agent, a fluorophore, or a luminophore.

In another embodiment of the present invention, there is a method of treating a tumor in situ in an individual comprising the steps of administering to the tumor a polymer composition that comprises a biocompatible polymer, a cross-linking composition that comprises a cross-linker, and the therapeutic agent, wherein the polymer composition and the cross-linking composition are administered to allow formation of a cross-linked polymer in situ at the tumor, which cross-linked polymer comprises the therapeutic agent. In a specific embodiment, the polymer composition comprises the therapeutic agent. In another specific embodiment, the polymer composition and the cross-linking composition are separately administered to the localized region. In an additional specific embodiment, the polymer composition and the cross-linking composition are administered to the localized region from separate containers, wherein a first container contains the polymer composition and a second container comprises the cross-linking composition. In an additional specific embodiment, the first and second containers are syringes. In another specific embodiment, the polymer composition and the cross-linking composition are administered to the region by means of a single container having at least two compartments, wherein one compartment comprises the polymer composition and another compartment comprises the cross-linking composition. In another specific embodiment, the polymer composition and the cross-linking composition are administered to the region by means of a single container having a hollow cylindrical compartment, wherein the polymer composition and cross-linking composition are administered separately through the compartment. In another specific embodiment, the separate administrations of the polymer composition and the cross-linking composition are by syringe. In an additional specific embodiment, the polymer composition and cross-linking compositions are administered separately from a syringe having at least two compartments.

In another specific embodiment, the polymer is a polysaccharide, a polyamino acid polymer, or a combination thereof. In an additional specific embodiment, the polymer is a polysaccharide, and the polysaccharide polymer is an alginate, hydroxycellulose, chondroitin, chitosan, hyaluronate, dextran or starch. In an additional specific embodiment, the polymer is a polyamino acid, and the polyamino acid is a polyglutamate or a polyaspartate. In an additional specific embodiment, the cross-linking agent is a salt of a divalent cation. In an additional specific embodiment, the divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{2+}$. In another specific embodiment, the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide. In an additional specific embodiment, the therapeutic agent is a drug, a hormone, a gene therapy composition, a radionuclide, a nutriceutical, or a combination thereof. In an additional specific embodiment, the therapeutic agent is a drug, and the drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, penicillin, erythromycin, amoxicillin, cefazolin, imipenem, aztreonam, sulbactam, linezolid, gentamicin, sulfamethoxazole, vancomycin, ciprofloxacin, fusidic acid, trimethoprim, metronidazole, clindamycin, mupirocin, amphotericin B, rifampin, fluconazoleor, or a combination thereof. In another specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2a}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof. In another specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf, erb, src, fins, jun, trk, ret, gsp, hst, bel abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, or a combination thereof. In an additional specific embodiment, the vector is a plasmid, an adenoviral vector, an adeno-associated viral vector, a retroviral vector, a liposome, or a combination thereof. In another specific embodiment, the therapeutic agent is a radionuclide, and the radionuclide is $^{188}Re$, $^{213}Bi$, $^{166}Ho$, $^{211}At$, or a combination thereof. In another specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, coenzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In an additional specific embodiment, the therapeutic agent further comprises a detectable identifier, wherein the detectable identifier is an X-ray contrasting agent, a CT contrasting agent, an MRI contrasting agent, a fluorophore, or a luminophore.

In another embodiment of the present invention there is a method of occluding an artery associated with a tumor in an individual comprising the step of administering to said tumor a polymer composition that comprises a biocompatible polymer, a cross-linking composition that comprises a cross-linker, wherein the polymer composition and the cross-linking composition are administered to allow formation of the cross-linked polymer in situ at the tumor. In a specific embodiment, the polymer composition further comprises a therapeutic agent. In an additional specific embodiment, the polymer composition and the cross-linking composition are separately administered to the tumor. In another specific embodiment, the polymer composition and the cross-linking composition are administered to the tumor from separate containers, wherein a first container contains the polymer composition and a second container comprises the cross-linking composition. In an additional specific embodiment, the first and second containers are syringes. In another specific embodiment, the polymer composition and the cross-linking composition are administered to the tumor by means of a single container having at least two compartments, wherein one compartment comprises the polymer composition and another compartment comprises the cross-linking composition. In another specific embodiment, the polymer composition and the cross-linking composition are administered to the region by means of a single container having a hollow cylindrical compartment, wherein the polymer composition and cross-linking composition are administered separately through the compartment. In an additional specific embodiment, the separate administrations of the polymer composition and the cross-linking composition are by syringe. In an additional specific embodiment, the polymer composition and cross-linking compositions are administered separately from a syringe having at least two compartments. In an additional specific embodiment, the polymer is a polysaccharide, a polyamino acid polymer, or a combination thereof. In another specific embodiment, the polymer is a polysaccharide, and the polysaccharide polymer is an alginate, hydroxycellulose, chondroitin, chitosan, hyaluronate, dextran or starch. In another specific embodiment, the polymer is a polyamino acid, and the polyamino acid is a polyglutamate or a polyaspartate. In another specific embodiment, the cross-linking agent is a salt of a divalent cation. In another specific embodiment, the divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{1+}$. In another specific embodiment, the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide.

In another specific embodiment, the therapeutic agent is a drug, a hormone, a gene therapy composition, a radionuclide, a nutriceutical, or a combination thereof. In an additional specific embodiment, the therapeutic agent is a drug, and the drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, penicillin, erythromycin, amoxicillin, erythromycin, cefazolin, imipenem, aztreonam, sulbactam, linezolid, gentamicin, sulfamethoxazole, vancomycin, ciprofloxacin, fusidic acid, trimethoprim, metronidazole, clindamycin, mupirocin, amphotericin B, rifampin, fluconazoleor, or a combination thereof. In an additional specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2a}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof. In an additional specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, or a combination thereof. In a specific embodiment, the vector is a plasmid, an adenoviral vector, an adeno-associated viral vector, a retroviral vector, a liposome, and a combination thereof. In an additional specific embodiment, the therapeutic agent is a radionuclide, and the radionuclide is $^{188}$Re, $^{213}$Bi, $^{166}$Ho, $^{211}$At, or a combination thereof. In another specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrur, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pan d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In a specific embodiment, the therapeutic agent further comprises a detectable identifier, wherein the detectable identifier is an X-ray contrasting agent, a CT contrasting agent, an MRI contrasting agent, a fluorophore, or a luminophore. In an additional specific embodiment, the administration step occurs through a catheter.

In an embodiment of the present invention there is a method of providing a slow-release hydrogel composition in situ to a tumor in an individual comprising administering to said tumor a polymer composition that comprises a biocompatible polymer, a cross-linking composition that comprises a cross-linker, and the therapeutic agent, wherein the polymer composition and the cross-linking composition are administered to allow formation of the cross-linked polymer in situ at the tumor, which cross-linked polymer comprises the therapeutic agent. In a specific embodiment, the polymer composition comprises the therapeutic agent. In an additional specific embodiment, the polymer composition and the cross-linking composition are separately administered to the tumor. In an additional specific embodiment, the polymer composition and the cross-linking composition are administered to the tumor from separate containers, wherein a first container contains the polymer composition and a second container comprises the cross-linking composition.

In an additional specific embodiment, the first and second containers are syringes. In another specific embodiment, the polymer composition and the cross-linking composition are administered to said region by means of a single container having at least two compartments, wherein one compartment comprises the polymer composition and another compartment comprises the cross-linking composition. In an additional specific embodiment, the polymer composition and cross-linking compositions are administered separately from a syringe having at least two compartments.

In another specific embodiment, the polymer is a polysaccharide, a polyamino acid polymer, or a combination thereof. In an additional specific embodiment, the polymer is a polysaccharide, and the polysaccharide polymer is an alginate, hydroxycellulose, chondroitin, chitosan, hyaluronate, dextran, or starch. In an additional specific embodiment, the polymer is a polyamino acid, and the polyamino acid is a polyglutamate or a polyaspartate. In an additional specific embodiment, the cross-linking agent is a salt of a divalent cation. In another specific embodiment, the divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{2+}$. In another specific embodiment, the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide. In another specific embodiment, therapeutic agent is a drug, a hormone, a gene therapy composition, a radionuclide, a nutriceutical, or a combination thereof. In an additional specific embodiment, the therapeutic agent is a drug, and the drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, penicillin, erythromycin, amoxicillin, erythromycin, cefazolin, imipenem, aztreonam, sulbactam, linezolid, gentamicin, sulfamethoxazole, vancomycin, ciprofloxacin, fusidic acid, trimethoprim, metronidazole, clindamycin, mupirocin, amphotericin B, rifampin, fluconazoleor, or a combination thereof.

In another specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2\alpha}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof.

In an additional specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, or a combination thereof.

In an additional specific embodiment, the vector is a plasmid, an adenoviral vector, an adeno-associated viral vector, a retroviral vector, a liposome, or a combination thereof. In another specific embodiment, the therapeutic agent is a radionuclide, and the radionuclide is $^{188}Re$, $^{213}Bi$, $^{166}Ho$, $^{211}At$, or a combination thereof. In an additional specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In another specific embodiment, the therapeutic agent further comprises a detectable identifier, wherein the detectable identifier is an X-ray contrasting agent, a CT contrasting agent, an MRI contrasting agent, a fluorophore, or a luminophore.

In an additional embodiment of the present invention, there is a kit for treating a tumor in situ in an individual comprising, in a suitable containing means a first container having a polymer composition; and a second container having a cross-linking composition. In a specific embodiment, the polymer composition further comprises a therapeutic agent. In another specific embodiment, the polymer is a polysaccharide, a polyamino acid polymer, or a combination thereof. In an additional specific embodiment, the polymer is a polysaccharide, and the polysaccharide polymer is alginate, hydroxycellulose, chondroitin, chitosan, or hyaluronate. In an additional specific embodiment, the polymer is a polyamino acid polymer, and the polyamino acid polymer is polyglutamate or polyaspartate. In an additional specific embodiment, the cross-linking agent is a salt of a divalent cation. In a specific embodiment, the divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{2+}$. In another specific embodiment the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide. In an additional specific embodiment, the therapeutic agent is an anticancer drug, a hormone, a gene therapy composition, a radionuclide, a nutriceutical, or a combination thereof. In an additional specific embodiment, the therapeutic agent is an anticancer drug, and the anticancer drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, or a combination thereof. In an additional specific embodiment, the therapeutic agent is a radionuclide, and the radionuclide is $^{188}$Re, $^{166}$Ho, $^{213}$Bi, $^{211}$At, or a combination thereof. In another specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, and a combination thereof. In an additional specific embodiment, the vector is a plasmid, an adenoviral vector, an adeno-associated viral vector, a retroviral vector, a liposome, or a combination thereof. In another specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2\alpha}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof. In another specific embodiment, the therapeutic agent is a radionuclide, and the radionuclide is $^{188}$Re, $^{213}$Bi, $^{166}$Ho, $^{211}$At, or a combination thereof. In an additional specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, *gymnema*, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In another specific embodiment, the therapeutic agent further comprises a detectable identifier, and the detectable identifier is an X-ray contrasting agent, a CT contrasting agent, an MRI contrasting agent, a fluorophore, or a luminophore.

In an additional embodiment of the present invention there is a kit for occluding an artery associated with a tumor in an individual comprising, in a suitable containing means a first container having a polymer composition; and a second container having a cross-linking composition. In a specific embodiment, the polymer composition further comprises a therapeutic agent. In another specific embodiment, the polymer is a polysaccharide, a polyamino acid polymer, or a combination thereof. In an additional specific embodiment, the polymer is a polysaccharide, and the polysaccharide polymer is alginate, hydroxycellulose, chondroitin, chitosan, or hyaluronate. In another specific embodiment, the polymer is a polyamino acid polymer, and the polyamino acid polymer is polyglutamate or polyaspartate. In a specific embodiment, the cross-linking agent is a salt of a divalent cation. In an additional specific embodiment, the divalent cation is $Ca^{2+}$, $Mg^{2+}$, $Mn^{2+}$, $Cu^{2+}$, $Cr^{2+}$, $Sr^{2+}$, $Zn^+$, $Ra^{2+}$, or $Be^{2+}$. In another specific embodiment, the salt of a divalent cation is calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide. In another specific embodiment, the therapeutic agent is an anticancer drug, a hormone, a gene therapy composition, a radionuclide, a nutriceutical, or a combination thereof. In an additional specific embodiment, the therapeutic agent is an anticancer drug, and the anticancer drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, or a combination thereof. In an additional specific embodiment, the therapeutic agent is a radionuclide, and the radionuclide is $^{188}Re$, $^{166}Ho$, $^{213}Bi$, $^{211}At$, or a combination thereof. In another specific embodiment, the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-1, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, and a combination thereof. In an additional specific embodiment, the vector is a plasmid, an adenoviral vector, an adeno-associated viral vector, a retroviral vector, a liposome, or a combination thereof. In another specific embodiment, the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_{2\alpha}$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin $D_3$, or a combination thereof. In an additional specific embodiment, the therapeutic agent is a radionuclide, and the radionuclide is $^{188}Re$, $^{213}Bi$, $^{166}Ho$, $^{211}At$, or a combination thereof. In an additional specific embodiment, the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, *garcinia* HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract. In another specific embodiment, the therapeutic agent further comprises a detectable identifier, and the detectable identifier is an X-ray contrasting agent, a CT contrasting agent, an MRI contrasting agent, a fluorophore, or a luminophore.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 9 shows tumor growth in mammary tumor-bearing rats in response to Re-188 treatment.

DESCRIPTION OF THE INVENTION

I. Definitions

Figure 1:
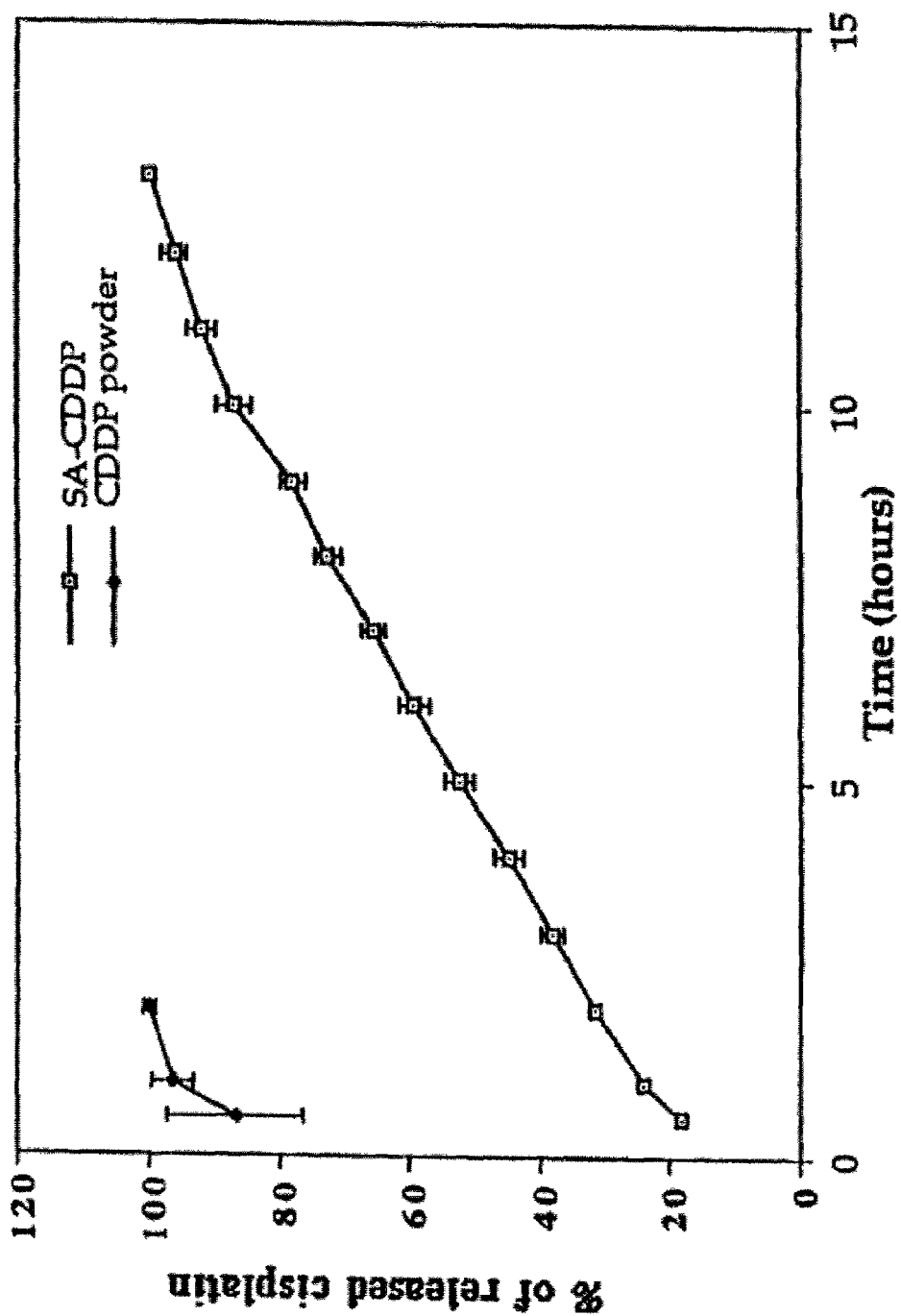
FIG. 1 illustrates in vitro slow release of cisplatin from alginate beads.

The term "anticancer drug" as used herein is defined as a drug for the treatment of cancer, such as for a solid tumor. The anticancer drug preferably reduces the size of the tumor, inhibits or prevents growth or metastases of the tumor, and/or eliminates the tumor.

The term "brachytherapy" as used herein is defined as insertion of a radioactive source into a patient in the form of tiny pellets, or seeds, which are implanted directly into a tumor-containing organ.

The term "cross-linking agent" as used herein is defined as an entity which creates chemical bonds, called cross links, between two separate molecules. In a specific embodiment, the cross-linking agent is a salt of a divalent cation. In a preferred embodiment, the cross-linking agent is calcium chloride. A cross-linking composition is a composition containing a cross-linking agent.

The term "drug" as used herein is defined as a compound which aids in the treatment of disease or medical condition or which controls or improves any physiological or pathological condition associated with the disease or medical condition. In a specific embodiment, the drug is an anticancer drug.

The term "hydrogel" as used herein is defined as a composition generated in situ in a body from a water-soluble biodegradable and biocompatible polymer and a cross linking agent.

The term "in situ" as used herein is defined as restricted to a specific site within a body without substantial invasion of surrounding tissues.

The term "local regional treatment" as used herein is defined as providing therapy to a specific and defined area of a body. In a preferred embodiment, the therapy is restricted primarily to this area and does not extend to nearby areas or tissues. In another preferred embodiment, the region is a solid tumor.

The term "nutriceutical" as used herein is a herb, medicinal plant, or diet-originated compound such as those used traditionally used in treatment of disease or a medical condition.

The term "polyamino acid" as used herein is defined as a polymer having multiple repeating units of the same amino acid. In specific embodiments, the polyamino acid is polyglutamate or polyaspartate.

The term "polymer" as used herein is defined as a compound comprising a linear arrangement of simpler repeating molecules. In a specific embodiment, the polymer is a polysaccharide or a polyamino acid. In a preferred embodiment, the polymer is a biodegradable and biocompatible polymer.

The term "polysaccharide" as used herein is defined as a carbohydrate comprising multiple monosaccharide units. A monosaccharide is a simple sugar unable to be decomposed by hydrolysis and generally has the formula $CH_2O$.

The term "radionuclide" as used herein is defined as a radioactive nuclide (a species of atom able to exist for a measurable lifetime and distinguished by its charge, mass, number, and quantum state of the nucleus) which, in specific embodiments, disintegrates with emission of corpuscular or electromagnetic radiations. The term may be used interchangeably with the term "radioisotope".

The term "therapeutic agent" as used herein is defined as an agent which provides treatment for a disease or medical condition. The agent in a specific embodiment improves at least one symptom or parameter of the disease or medical condition. For instance, in tumor therapy, the therapeutic agent reduces the size of the tumor, inhibits or prevents growth or metastases of the tumor, or eliminates the tumor. Examples include a drug, such as an anticancer drug, a gene therapy composition, a radionuclide, a hormone, a nutriceutical, or a combination thereof.

The term "tumor" as used herein is defined as an uncontrolled and progressive growth of cells in a tissue. A skilled artisan is aware other synonymous terms exist, such as neoplasm or malignancy. In a specific embodiment, the tumor is a solid tumor. In other specific embodiments, the tumor derives, either primarily or as a metastatic form, from cancers such as of the liver, prostate, pancreas, head and neck, breast, brain, colon, adenoid, oral, skin, lung, testes, ovaries, cervix, endometrium, bladder, stomach, and epithelium (such as a wart).

As used herein the specification, "a" or "an" may mean one or more. As used herein in the claim(s), when used in conjunction with the word "comprising", the words "a" or "an" may mean one or more than one. As used herein "another" may mean at least a second or more.

II. The Present Invention

The present invention is directed to a cost-effective and efficient local regional treatment technique that can be used for gene therapy, brachytherapy, transcatheter arterial chemoembolization (TACE) and/or intralesional injection. The methods of the present invention generally regard utilizing a polymer, such as a polysaccharide or a polyamino acid, to carry and dispense a therapeutic agent, such as anticancer drugs, radionuclides, and/or gene therapy compositions intralesionally into tumor tissue or tumor vessels. A cross linker is administered therein to generate hydrogel in situ. In a specific embodiment, this occurs subsequent to administration of the polymer composition. In another specific embodiment, the therapeutic compositions and the cross linker are administered by injection, such as with two separate syringes, or with one syringe having two needles. Preferably, the procedure is monitored by, for instance, ultrasound, computer tomography (CT) scan, X-ray, or magnetic resonance imaging. Thus, non-surgical methods are employed for tumor treatment because the hydrogel is generated within the tumor itself. The current methods in the art for administering an agent are unwieldy and utilize generation of relatively large amounts of therapeutic polymer compositions ex vivo, followed by post-processing procedures to obtain beads of the appropriate size for injection that wastes significant amounts of polymer and therapeutic agents, which are costly. Thus, the in situ methods of the present invention allow correct dosing, are relatively easy to perform, and are cost-effective, generating little waste of expensive chemotherapeutics.

A. Transcatheter Arterial Chemoembolization

In a TACE-related specific embodiment of the present invention, the hydrogel, which may also contain a therapeutic agent, is generated within the tumor by injection of the composition and cross linker into an artery which nourishes the tumor. This allows the hydrogel to occlude tumor vessels and preferably provides complete occlusion of tumor vessels. Preferably, the vessel remains blocked for at least about six hours.

B. Peritumor/Intralesional Injection

In a peritumor/intralesional injection specific embodiment of the present invention, the methods are useful to directly contact and treat tumor tissue by directly injecting the composition(s) into the tumor wherein the subsequently-formed hydrogel comprises a therapeutic agent subject to sustained release from the hydrogel.

In specific embodiments directed to radionuclide therapy, either polysaccharide or polyamino acid is labeled with a radionuclide, although in a preferred embodiment polyamino acids are labeled with a radionuclide. The radionuclide therapy of the present invention provides greater loading, ease of process, and reduced cost compared to brachytherapy methods used presently in the art. In a specific embodiment, combinations of radionuclides (alpha and/or beta or gamma emitters) are utilized as cocktail radiotherapy with methods of the present invention. In another specific embodiment, the radionuclide therapy of the present invention, in contrast to the anticancer drug therapy embodiment of the present invention, does not allow leakage of the isotope from the matrix due to ionic bonds formed between the radionuclide and the polymer.

In a specific embodiment, the methods of the present invention are particularly useful for tumors where removal by surgery is not a viable option.

C. Specific Embodiments

1. Polymers

Polymers of the present invention, in a specific embodiment, act as carriers for dispensing the therapeutic agent in situ. Polymers are well known in the art and are preferably water soluble, biocompatible, and biodegradable. In a specific embodiment, the polymer degrades in no less than about 1 day and no more than about 30 days. However, it is unnecessary to be biodegradable in the embodiment wherein a radionuclide is the therapeutic agent given that ionic bonds formed between the radionuclide and hydroxy groups of the polymer retain the radionuclide within the polymer composition.

A skilled artisan is knowledgeable about polymers suitable for utilization in the methods of the present invention. Particularly, in the specific embodiment wherein a polymer/therapeutic agent is administered into a solid tumor or localized region of an individual and is followed by an administration of a cross-linking agent, polymers, polymer concentrations, cross-linking agents, and cross-linking agent concentrations are selected which facilitate quick polymerization. "Quick polymerization" as used herein is defined as polymerization which is rapid enough to retain all compositions within the solid tumor or localized region of interest without significant leakage to surrounding tissues.

In the specific embodiment wherein a polymer/therapeutic agent and cross-linking agent are administered into a solid tumor or localized region of an individual substantially simultaneously, such as from a single injection from a syringe having at least one compartment, the polymers, polymer concentrations, cross-linking agents, and cross-linking agent concentrations are selected which facilitate relatively slow polymerization. "Slow polymerization" as used herein is defined as polymerization which is rapid enough to retain all compositions within the solid tumor or localized region of interest without significant leakage to surrounding tissues but is slow enough to permit efficient administration of the compositions into the tumor or region. That is, polymerization must occur slowly enough that polymerization does not occur within the administration apparatus, such as the syringe.

(a) Polysaccharides

Many polysaccharides are known in the art and are useful in the present invention as long as they are capable of retaining a therapeutic agent, are compatible with the tissue and body of an individual to be treated, are suitable for injection via a syringe, and are able to be cross-linked with an appropriate cross-linking agent, such as a salt of a divalent cation. The polysaccharide preferably breaks down over time, causing release of the therapeutic agent directly into the tumor tissue. However, if the therapeutic agent is a radionuclide, the ionic bonds formed between the radionuclide and the polysaccharide preferably prevent leakage of the radionuclide from the polysaccharide hydrogel composition. The polysaccharides are preferably water-soluble, biocompatible and biodegradable.

Specific examples of polysaccharides include sodium alginate, hydroxycellulose, chondroitin, chitosan, hyaluronate, dextran and starch. A specific embodiment regarding use of sodium alginate in methods of the present invention follows.

Sodium alginate (SA) is a hydrophilic gelling polysaccharide extracted from giant brown seaweed that has previously been described as having satisfactory hemocompatibility. Alginate beads or microspheres are instantly formed by cross-linking with calcium chloride. The reaction is simple and fast. Due to slow blood flow through the tortuous and irregular neoplastic vessels, which often lack both a muscular layer and elastic lamellae, the injected SA solution is easier to fill tumor vessels. Upon injection of calcium chloride locally into the tumor, the calcium ion is diffused in the interstitial space and reacts with SA. Alginate hydrogel is generated instantly in the tumor vasculature and sinusoids. This causes: 1) "concrete" occlusion of the vasculature in the tumor by alginate hydrogel loaded with anticancer drugs; 2) because no calcium ion is injected in the normal liver tissue around the tumor, embolization is unlikely to occur in there, and SA is eventually washed out. In a preferred embodiment of the present invention, there is highly selective complete TACE for cancer therapy by using SA. When SA is used in TACE, an increased anticancer effect, decreased liver tissue damage, and decreased side effects are demonstrated. In summary, the advantages of using SA in TACE include: 1) Concrete chemoembolization in tumor: in a specific embodiment, alginate hydrogel completely fills tumor vessels to cause occlusion, which also reduces the chance of formation of new collateral vessels from tumor; 2) Homogenous drug distribution in the tumor: in another specific embodiment, SA solution fully occupies tumor vascular space, including capillaries and sinusoids, thus providing a better drug-to-tumor cell interaction; 3) Increased anticancer drug level and retention time in the tumor: there is almost no blood flow in the tumor after concrete occlusion, and washing the drugs out of the tumor would be slow because of the sustained-release property of alginate hydrogel; 4) Selective chemoembolization: alginate cross-linking is restricted in the tumor following the intra-tumoral injection of calcium chloride, and less embolization occurs in normal tissue. These results can be achieved by ultrasound-guided target injection; 5) Low toxicity and low cost: SA and calcium chloride are low in toxicity, with no toxic material produced in the cross-linking reaction, and SA is an inexpensive (approximately $20/100 g); 6) SA and other polysaccharides (e.g. hydroxycellulose, chondroitin, chitosan) are also good carriers for delivering radionuclides or other agents.

(b) Polyamino Acids

In a specific embodiment of the present invention, polyamino acids are utilized as the polymer component of the hydrogel composition. In a further specific embodiment, the polyamino acid is polyaspartate or polyglutamate. In a preferred embodiment, a radionuclide of the present invention is combined with a polyamino acid in the hydrogel.

Many polyamino acids are known in the art and are useful in the present invention as long as they are capable of retaining a therapeutic agent, are compatible with the tissue and body of an individual to be treated, are suitable for injection via a syringe, and are able to be cross-linked with an appropriate cross-linking agent, such as a salt of a divalent cation. The polyamino acid preferably breaks down over time, causing release of the therapeutic agent directly into the tumor tissue. However, if the therapeutic agent is a radionuclide, the ionic bonds formed between the radionuclide and the polyamino acid preferably prevent leakage of the radionuclide from the polysaccharide hydrogel composition.

2. Cross-Linking Agents

In a specific embodiment of the present invention, a cross-linking agent is utilized to cross link the polymer to the therapeutic agent and is injected into a tumor following injection of the polymer/therapeutic agent composition. In a preferred embodiment, the cross-linking agent is a salt of a divalent cation. Divalent cations include calcium, magnesium, copper, manganese, chromium, zinc, radium, barium, beryllium, and strontium. Salts include those of chloride, sulfate, phosphate, carbonate, chlorate, fluoride, and bromide. In a preferred embodiment, the cross-linking agent is at about 3% in solution and is soluble in aqueous solutions such as water.

3. Therapeutic Agents

In a preferred embodiment, a therapeutic agent such as a drug, including an anticancer drug, a radionuclide, a gene therapy composition, a hormone, a nutriceutical, and a combination thereof are administered by methods of the present invention for local regional treatment in an individual. In a specific embodiment, they are administered with a polymer. Given the heterogeneous nature of a tumor, it is beneficial and preferred to employ more than one type of therapeutic agent, or multiple species within a type of therapeutic agent, to provide therapy to the tumor in its entirety.

In one embodiment, the therapeutic agent further comprises a detectable identifier, such as an X-ray contrasting agent, a computer tomography (CT) contrasting agent, a magnetic resonance imaging (MRI) contrasting agent, a fluorophore, or a luminophore. Such a detectable identifier permits monitoring of the therapeutic agent, such as with unintentional leakage into surrounding tissue and/or to mark a tumor which has been injected.

(a) Drugs

In a specific embodiment of the present invention, the polymer is associated with a drug for local regional treatment in an individual.

(1) Chemotherapeutic Drug

In a preferred embodiment, the drug is an anticancer drug, also known in the art as a chemotherapeutic agent. These can be, for example, agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxy-acetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced crosslinking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg., 20 mg., or 10 mg. I.V., the maximal serum concentrations were 2.4 mg./mL, 1.7 mg./mL, and 0.52 mg./mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D

Actinomycin D (Dactinomycin) [50–76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Bleomycin

Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

(2) Miscellaneous Agents

Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15–20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

VP16

VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200–250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor

Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

(3) Plant Alkaloids

Taxol

Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can alos be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine

When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

(4) Alkylating Agents

Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15 th Edition, chapter 61. Some variation in dosage will necessarily occur depending on the condition of the subject being treated. The person responsible for administration will, in any event, determine the appropriate dose for the individual subject.

Melphalan

Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15 th Edition, chapter 61, incorporate herein as a reference, for details on doses for administration.

Chlorambucil

Chlorambucil (also known as leukeran) was first synthesized by Everett et al. (1953). It is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6–1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remingtons Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

4. Non-Chemotherapeutic Drugs

In an alternative embodiment, the local regional treatment provided by the methods of the present invention employ another type of drug to provide therapy to a specific region of an individual. For instance, in a localized region comprising, for example, an abscess or boil, an antibiotic may be utilized. Another example would include administration of an antibiotic or pain medication, such as in an opening remaining from extraction of a tooth. An additional example would be administration of bone morphogenetic factors, such as into a degenerative bone site. In an alternative embodiment, a compound to decrease bone content, dissolve bone, or the like is administered to a bone spur. In another specific embodiment, a compound is administered to a corn, such as on a foot, for reducing its size or completely eliminating it.

The term "antibiotics" as used herein is defined as a substance that inhibits the growth of microorganisms without damage to the host. For example, the antibiotic may inhibit cell wall synthesis, protein synthesis, nucleic acid synthesis, or alter cell membrane function.

Classes of antibiotics that can possibly be used include, but are not limited to, macrolides (i.e., erythromycin), penicillins (i.e., nafeillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, polyenes (i.e., amphotericin B), rifamycins (i.e., rifampin), and azoles (i.e., fluconazole).

Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104 herein incorporated by reference will readily suggest themselves to those of ordinary skill in the art.

(a) Radionuclides

In a specific embodiment of the present invention, the polymer is associated with a radionuclide for local regional treatment in an individual. In a preferred embodiment, the radionuclide is an inorganic metal. Examples include $^{188}$Re, $^{213}$Bi, $^{166}$Ho, and $^{211}$At. The radionuclide preferably has a half-life which does not exceed the time it takes for the eventual breakdown of the hydrogel so that other tissues in the patient are not adversely affected by the radionuclide. Half-lives of different radionuclides are known in the art and are also available in standard texts or on the world wide web (http://physics.nist.gov/PhysRefData/Halflife/halflife.html). In a specific embodiment, a radionuclide cocktail is administered having more than one radionuclide. In a further specific embodiment, alpha, beta and/or gamma, or any combination thereof, emitters are included in the cocktail. A skilled artisan is aware that gamma emitters may be used to facilitate visualization of an agent, but that care must be taken to prevent utilizing quantities which would destroy surrounding healthy tissue. In a specific embodiment, the terms "radionuclide therapy" or "radiopharmaceutical" or "internal radiation therapy" are used interchangeably.

The polymer of the methods of the present invention contains many hydroxy groups which permit ionic bond formation and retain the radionuclide within the hydrogel composition.

A skilled artisan is aware that there are multiple modes of generating a radionuclide, and the methods of the present invention are not limited by the mode of generation of the radionuclide itself.

(b) Gene Therapy Compositions

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

(c) Hormones

In an embodiment of the present invention, wherein the local regional treatment provided by the methods of the present invention is for an application other than for a solid tumor, hormones may be employed. As an example, luteinizing hormone releasing hormone (LHRH) is administered to the endometrium of an individual affected with endometriosis.

Examples of hormones which may be used in the present invention include luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin $I_2$, prostaglandin $E_2$, prostaglandin $F_2a$, relaxin, serotonin, serum thymic factor, substance P, thromboxane $A_2$, thymopoietin, thymosina, thyrotopin (thyroid stimulating hormone; TSH), thyrotropin releasing hormone, thyroxine, triiodothyronine, urogastrone, vasoactive intestinal peptide, vasotocin, or vitamin $D_3$.

(d) Nutriceuticals

In another embodiment of the present invention, a nutriceutical is administered in situ to a localized region of an individual. Examples of nutriceuticals include arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chlorella, chondroitin sulfate, chromium yeast, citrus aurantium, citrus seed extract, co-enzyme Q10, colostrum, cordyceps, cranberry, creatine monohydrate, devil's claw, DHEA, DMG, dong quai, Echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, or yohimbe bark extract.

III. Combination Treatments

In order to increase the effectiveness of the methods of the present invention, it may be desirable to combine the anti-cancer compositions with other agents also effective in the treatment of hyperproliferative disease. Such combination treatments may occur within administration of the therapeutic methods of the present invention, for instance combining gene therapy and an anticancer drug within the same in situ injection protocol. Alternatively, combination treatments may be utilized within the scope of the present invention by administering one or more therapeutic agents in situ by the methods of the present invention in addition to, for example, administering a therapeutic agent systemically.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the life span of a subject with cancer. More generally, these compositions and methods would be provided in a combined amount effective to kill or inhibit proliferation of the cell. This process may involve contacting the cells with an anticancer agent and multiple factor(s) at the same time. This may be achieved by contacting the cell with a single composition or pharmacological formulation that includes both agents, or by contacting the cell with two distinct compositions or formulations, at the same time, wherein one composition includes, for instance, an expression construct and the other includes the second agent(s), such as a radionuclide or anticancer drug.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that gene therapy could be used similarly in conjunction with chemotherapeutic, radiotherapeutic, or immunotherapeutic intervention, in addition to other pro-apoptotic or cell cycle regulating agents.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, gene therapy is "A" and the secondary agent, such as radio- or chemotherapy, is "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies with both chemical- and radiation-based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. In a preferred embodiment, the agent(s) is delivered into the solid tumor by the methods of the present invention to directly contact the cells of the solid tumor. To achieve cell killing or stasis, agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a secondary gene therapy in which a second therapeutic polynucleotide is administered before, after, or at the same time a first therapeutic polynucleotide encoding all of part of an anticancer polypeptide. Delivery of a vector encoding either a full length or truncated anticancer polypeptide in conjunction with a second vector encoding one of the following gene products will have a combined anti-hyperproliferative effect on target tissues. Alternatively, a single vector encoding both genes may be used. A variety of proteins are encompassed within the invention, some of which are described below.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., BCl$_{XL}$, Bcl$_W$, Bcl$_S$, Mcl-1, A1, Bfl-1) or counteract Bcl-2 function and promote cell death w (e.g., Bax, Bak, Bik, Bim, Bid, Bad, Harakiri).

4. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers. Immunomodulatory agents include tumor necrosis factor; interferon alpha, beta, and gamma; IL-2 and other cytokines; $F_{42}K$ and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 1

Oncogenes

| Gene | Source | Human Disease | Function |
| --- | --- | --- | --- |
| Growth Factors[1] | | | FGF family member |
| HST/KS | Transfection | | |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases[1,2] | | | |
| ERBB/HER | Avian erythroblastosis virus; ALV promoter insertion; amplified human tumors | Amplified, deleted squamous cell cancer; glioblastoma | EGF/TGF-α/ amphiregulin/ hetacellulin receptor |
| ERBB-2/NEU/HER-2 | Transfected from rat Glioblatoms | Amplified breast, ovarian, gastric cancers | Regulated by NDF/ heregulin and EGF-related factors |
| FMS | SM feline sarcoma virus | | CSF-1 receptor |
| KIT | HZ feline sarcoma virus | | MGF/Steel receptor hematopoieis |
| TRK | Transfection from human colon cancer | | NGF (nerve growth factor) receptor |
| MET | Transfection from human osteosarcoma | | Scatter factor/HGF receptor |
| RET | Translocations and point mutations | Sporadic thyroid cancer; familial medullary thyroid cancer; multiple endocrine neoplasias 2A and 2B | Orphan receptor Tyr kinase |
| ROS | URII avian sarcoma Virus | | Orphan receptor Tyr kinase |
| PDGF receptor | Translocation | Chronic myclomonocytic leukemia | TEL(ETS-like transcription factor)/ PDGF receptor gene fusion |
| TGF-β receptor | | Colon carcinoma mismatch mutation target | |

TABLE 1-continued

Oncogenes

| Gene | Source | Human Disease | Function |
|---|---|---|---|
| NONRECEPTOR TYROSINE KINASES[1] | | | |
| ABL | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES[1] | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling? |
| MISCELLANEOUS SIGNALING[1,3] | | | |
| BCL-2 | Translocation | B-cell lymphoma | Apoptosis |
| CBL | Mu Cas NS-1 V | | Tyrosine-phosphorylated RING finger interact Ab1 |
| CRK | CT1010 ASV | | Adapted SH2/SH3 interact Ab1 |
| DPC4 | Tumor suppressor | Pancreatic cancer | TGF-$\beta$-related signaling pathway |
| MAS | Transfection and Tumorigenicity | | Possible angiotensin receptor |
| NCK | | | Adaptor SH2/SH3 |
| GUANINE NUCLEOTIDE EXCHANGERS AND BINDING PROTEINS[3,4] | | | |
| BCR | | Translocated with ABL in CML | Exchanger; protein kinase |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS[1,5–9] | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |

TABLE 1-continued

Oncogenes

| Gene | Source | Human Disease | Function |
|---|---|---|---|
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGG/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE[10–21] | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| FHIT | Fragile site 3p14.2 | Lung carcinoma | Histidine triad-related diadenosine 5',3""-$P^1,P^4$ tetraphosphate asymmetric hydrolase |
| hMLI/MutL | | HNPCC | Mismatch repair; MutL homologue |
| hMSH2/MutS | | HNPCC | Mismatch repair; MutS homologue |
| hPMS1 | | HNPCC | Mismatch repair; MutL homologue |
| hPMS2 | | HNPCC | Mismatch repair; MutL homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |

TABLE 1-continued

Oncogenes

| Gene | Source | Human Disease | Function |
|---|---|---|---|
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

IV. Nucleic Acid-Based Expression Systems

In specific embodiments of the present invention, a gene therapy composition comprising a vector containing a nucleic acid expressing a therapeutic gene product is utilized. Specific embodiments of these vectors are hereafter discussed.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer imay be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Tables 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al.,1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1998 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al, 1998), murine epididymal retinoic acid-binding gene (Lareyre et al., 1999), human CD4 (Zhao-Emonet et al., 1998), mouse alpha2 (XI) collagen (Tsumaki, et al., 1998), DlA dopamine receptor gene (Lee, et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

V. Pharmaceutical Compositions

A. Pharmaceutically Acceptable Carriers

Aqueous compositions may be used in the present invention and comprise an effective amount of a therapeutic chemical compound or pharmaceutically acceptable salts thereof or a therapeutic protein, polypeptide, peptide, epitopic core region, inhibitor, and/or such like, dissolved and/or dispersed in a pharmaceutically acceptable carrier and/or aqueous medium. Aqueous compositions of gene therapy vectors expressing any therapeutic gene product are also contemplated.

The phrases "pharmaceutically and/or pharmacologically acceptable" refer to molecular entities and/or compositions that do not produce an adverse, allergic and/or other untoward reaction when administered to an animal as appropriate.

As used herein, "pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for injection into a solid tumor or into an artery. The preparation of an aqueous compositions that contain an effective amount of a therapeutic agent as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms. In a preferred embodiment, the dispersions are then mixed with a polymer for injection in situ into a solid tumor or localized region of an individual.

Therapeutic agents of the present invention can be formulated into a composition in a neutral and/or salt form. Pharmaceutically acceptable salts, include the acid addition salts (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine and/or the like. In terms of using peptide therapeutics as active ingredients, the technology of U.S. Pat. Nos. 4,608,251; 4,601,903; 4,599,231; 4,599,230; 4,596,792; and/or 4,578,770, each incorporated herein by reference, may be used.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15 th Edition, pages 1035–1038 and/or 1570–1580). Some variation in dosage will necessarily occur depending on the condition of the subject being treated. The person responsible for administration will, in any event, determine the appropriate dose for the individual subject.

The therapeutic agent may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

VI. Lipid Formulations and/or Nanocapsules

In certain embodiments, the use of lipid formulations and/or nanocapsules is contemplated for the introduction of a therapeutic agent into a solid tumor or localized region of an individual.

Nanocapsules can generally entrap compounds in a stable and/or reproducible way. To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and/or such particles may be easily made.

In a preferred embodiment of the invention, the therapeutic agent may be associated with a lipid. The therapeutic agent associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/therapeutic agent-associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

VII. Kits

Therapeutic kits of the present invention are kits comprising a therapeutic agent such as a drug, for example an anticancer drug, or a gene therapy composition. Although a radionuclide is preferably obtained by a skilled artisan from a source such as a nuclear pharmacy, in a specific embodiment the kit comprises a radionuclide.

Such kits will generally contain, in suitable container means, a pharmaceutically acceptable formulation of a therapeutic agent. The kit may have a single container means, and/or it may have distinct container means for each compound. The kit also further comprises a polymer, such as a polysaccharide or polyamino acid and a cross-linking agent. In a preferred embodiment, the polymer composition and the cross-linking composition are in separate containers.

In a specific embodiment, these containers are syringes. In another specific embodiment, a polymer composition and a cross-linking composition are contained in a syringe having at least two compartments.

When the components of the kit are provided in one and/or more liquid solutions, the liquid solution is an aqueous solution, with a sterile aqueous solution being particularly preferred. The therapeutic agent compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one syringe, vial, test tube, flask, bottle, and/or other container means, into which the therapeutic agent formulation(s) are placed, preferably, suitably allocated. The kits may also comprise a second container means for containing a sterile, pharmaceutically acceptable buffer and/or other diluent.

The kits of the present invention will also typically include a means for containing the syringes in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate therapeutic agent within the body of an animal. Such an instrument may be a syringe, pipette, forceps, and/or any such medically-approved delivery vehicle.

VIII. Delivery of the Hydrogel

In a preferred embodiment, a therapeutic agent and a polymer are administered to a site to be treated, such as a tumor site, followed by administration of a cross-linking agent. In a preferred embodiment, the polymer and therapeutic agent are administered concomitantly. In a specific embodiment, the polymer/therapeutic agent are administered by injection with one syringe, followed by administration of the cross-linking agent in a second injection with a second syringe. The injections are preferably administered under the guidance of, for instance, ultrasound technology. In an alternative embodiment, the polymer/therapeutic agent and cross-linking agent are administered from a single needle of a syringe having two separate compartments, or barrels, with one compartment containing the polymer composition and the other compartment containing the cross-linking agent. In another alternative embodiment, an introducing apparatus, such as a cannula or introducer, having at least one, and preferably one, needle is guided by ultrasound to a tumor site. The introducing apparatus has a hollow cylindrical compartment in which one syringe is inserted for introduction of the polymer/therapeutic agent composition, followed by insertion into the hollow compartment of a second syringe for introduction of the cross-linking agent composition. In this embodiment, there preferably is only one needle injection and accompanying ultrasound guidance.

Figure 7:
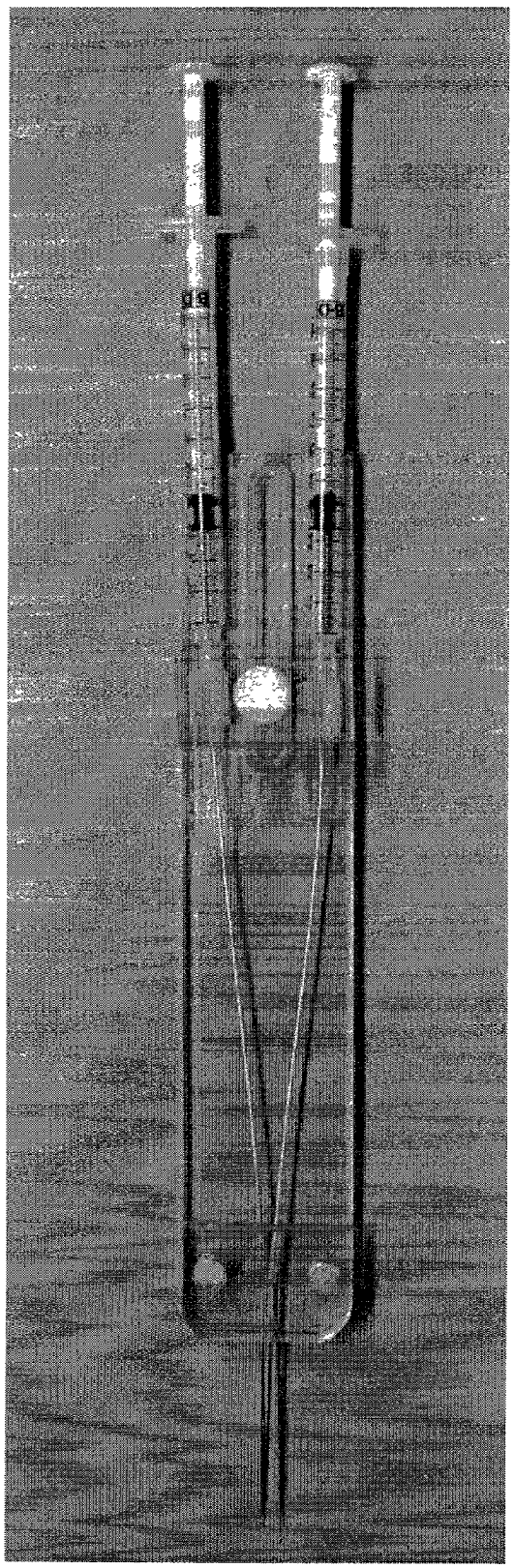
FIG. 7 illustrates one embodiment of a device for radionuclide therapy.
Figure 8:
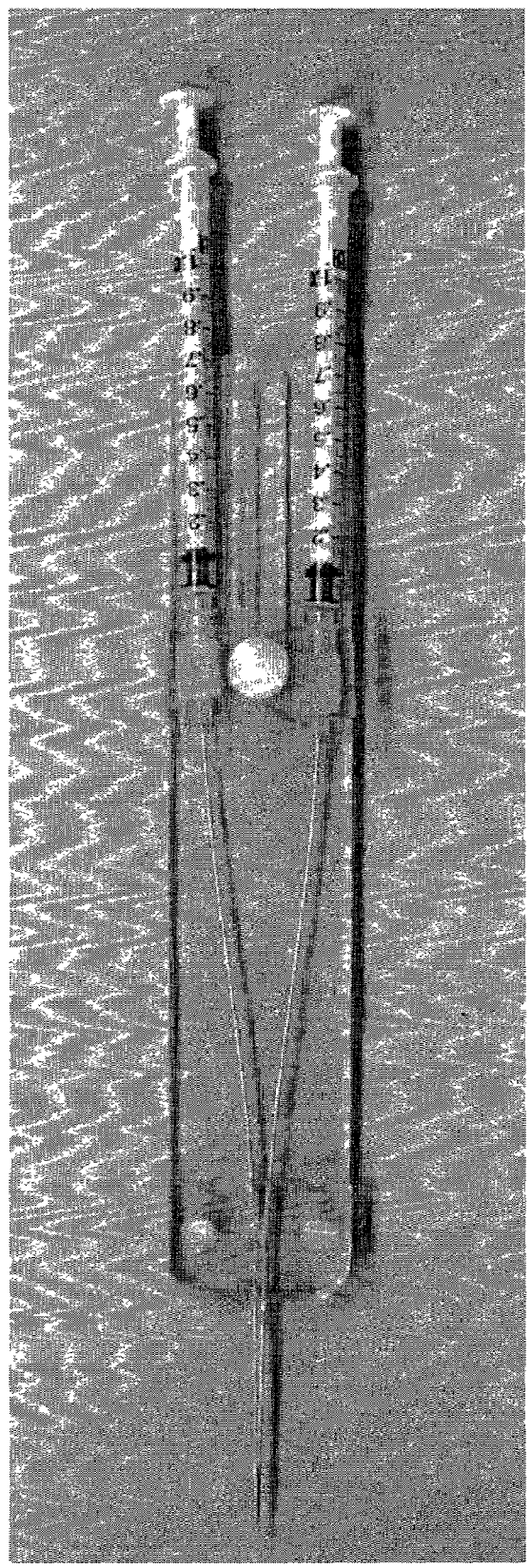
FIG. 8 illustrates another view of one embodiment of a device for radionuclide therapy.

In a specific embodiment, the hydrogel components are administered with a device such as is illustrated in FIGS. 7 and 8.

IX. EXAMPLES

The following examples are offered by way of example and are not intended to limit the scope of the invention in any manner.

Example 1

In Vitro Slow Release of Cisplatin from Alginate Beads

To study in vitro slow release of an anticancer drug from a polymer, the anticancer drug cisplatin and the polymer sodium alginate were tested for slow release of the drug. Cisplatin-loaded alginate beads (SA-CDDP) were formed instantly and then incubated in phosphate-buffered saline (PBS) in tubes at 37° C. Cisplatin was completely released from the alginate beads in 15 hours, which is considerably slower than the release time (within 2.5 hours) of cisplatin powder only (control) (FIG. 1).

Example 2

Intratumoral Injection of Sodium Alginate-Cisplatin (SA-CDDP)

Rats with mammary tumor (in the thighs, tumor size is 2.5×2.0 cm, n=5) were used in this experiment. SA-CDDP (5.4 mg cisplatin/ml) was made by suspending cisplatin in SA. A skilled artisan is aware of different parameters which affect dosages required to treat a particular tumor, such as size of the tumor, tumor type, and the like.

Figure 2:
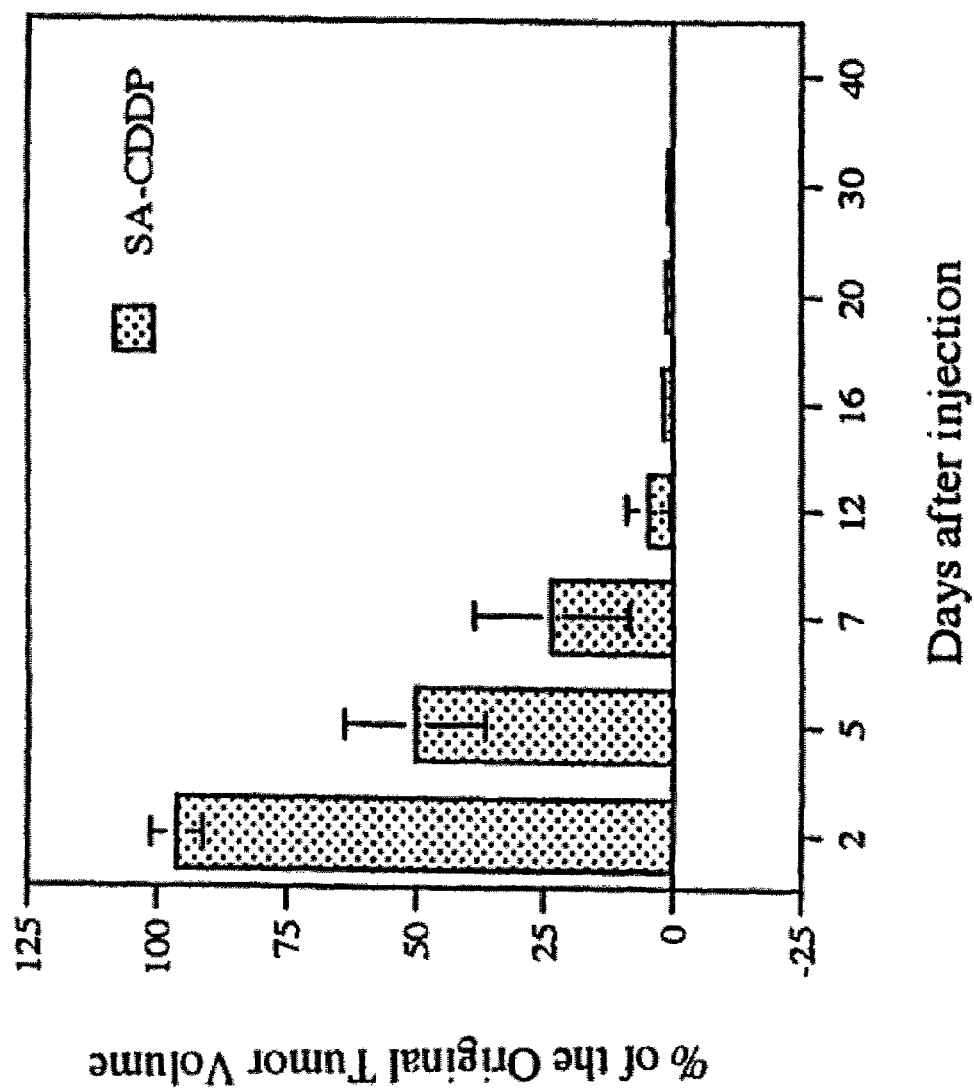
FIG. 2 demonstrates anticancer effect of intratumoral injection of sodium alginate/cisplatin (SA-CDDP) (3 mg/kg) in rats.

The SA-CDDP (0.1 ml; cisplatin dose was 3 mg/kg body weight) was injected directly into the tumors through 27 G needles. In a preferred embodiment, about 1 g SA is used per injection. Calcium chloride (8% in water) was then injected into the same place to form cisplatin-loaded alginate beads in the tumors. The tumor size was measured to determine the anticancer effect, and the blood chemical assay (blood urea nitrogen [BUN] and serum creatinine) were performed to detect renal toxicity. After injection, tumor volume decreased as a function of time (FIG. 2). No tumor relapse had occurred in the rats 5 months after treatment.

Figure 3:
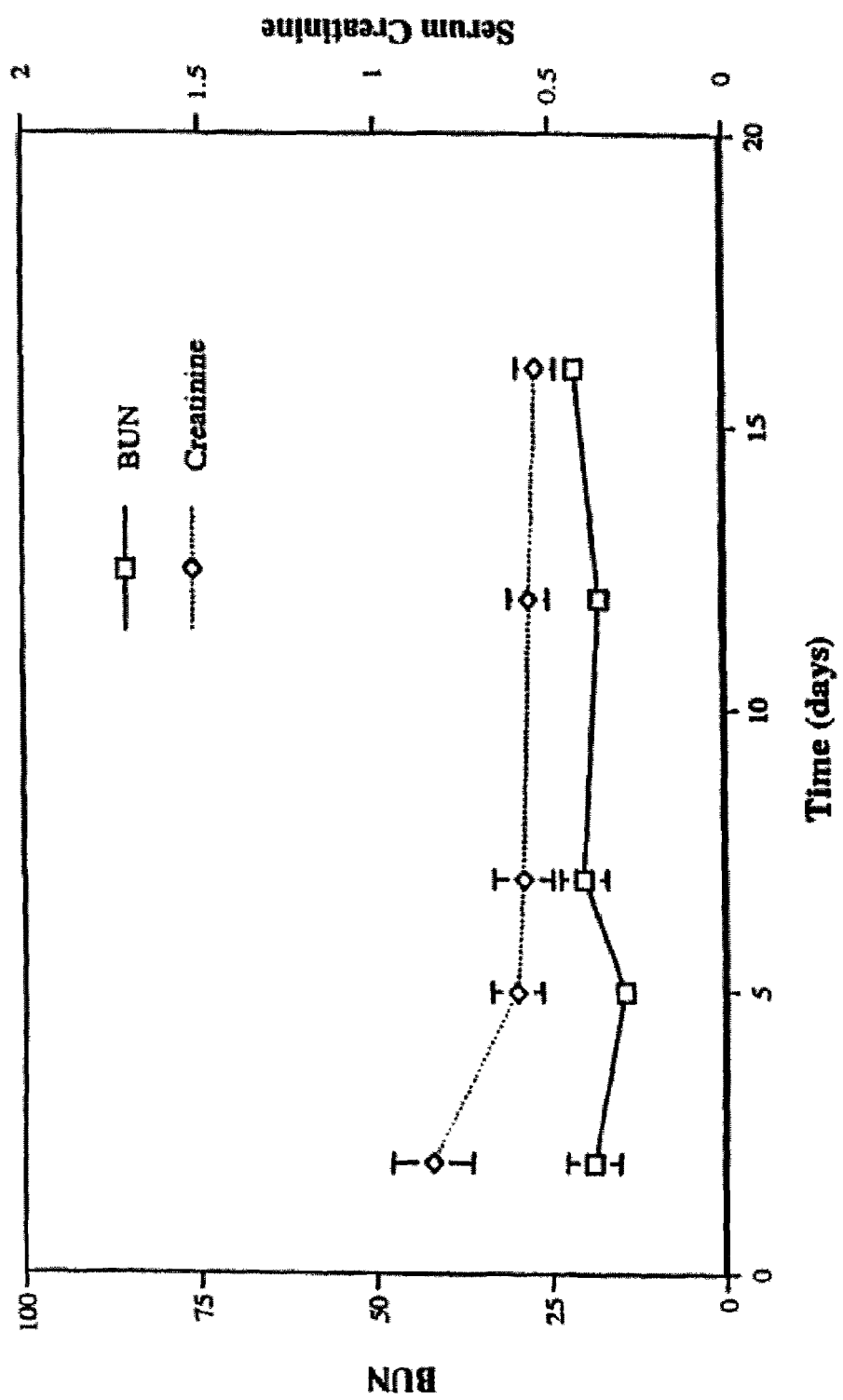
FIG. 3 illustrates changes in blood urea nitrogen (BUN) and creatinine in rats after intratumoral injection of SA-CDDP (3 mg/kg).

Tests for renal toxicity are demonstrated in FIG. 3. BUN and serum creatinine levels after intratumoral injection of SA-CDDP were in the normal range. On day 40, BUN in five experimental rats and five healthy rats (control) were 18.30±1.51 mg/dl and 17.88±2.24 mg/dl, respectively. There was no statistical significance (p>0.05) between the two. Serum creatinine levels were the same as in both experimental and control rats (0.6 mg/dl). In rats treated with CDDP intratumorally, a clear nephrotoxicity was observed as evidenced by increased BUN and creatinine levels (Table 4).

TABLE 4

EFFECT OF INTRATUMORAL INJECTION OF CDDP (3 MG/KD) ON BLOOD UREA NITROGEN AND CREATININE IN BREAST TUMOR-BEARING RATS

| TIME (days) | BUN (mg/dL) |
|---|---|
| 2 | 56.21 |
| 5 | 246.42 |
| 7 | 152.35 |
| 16 | 41.75 |

TABLE 4-continued

EFFECT OF INTRATUMORAL INJECTION OF CDDP (3 MG/KD) ON BLOOD UREA NITROGEN AND CREATININE IN BREAST TUMOR-BEARING RATS

| TIME (days) | SERUM CREATININE (mg/dL) |
|---|---|
| 2 | 1.5 |
| 5 | 7.03 |
| 7 | 2.4 |
| 16 | 0.7 |

In a preferred embodiment, the polymeric/therapeutic agent composition is injected prior to injection of the cross linker because the cross linker used is a small water soluble molecule which could diffuse through tumor vasculature beds.

Example 3

Pharmacokinetic Evaluation of Hydrogel in Tumor-Bearing Rabbits

To test for sustained release assay of anticancer drugs, rabbits are xenografted with mammary tumor cells (VX-2). Polysaccharide/anticancer drugs along with a cross linker are administered intralesionally. At various time intervals, blood samples are collected. Analysis of anticancer drug therapy is performed.

A stability assay of radionuclide/polyamino acids matrix is performed. Tumor-bearing rabbits are administered polyamino acids chelated with isotopes. At various time intervals, blood samples are collected. Analysis of radionuclide therapy is performed.

Example 4

Anticancer Effect of Tace with Polysaccharide/Anticancer Agents in Tumor-Bearing Rabbits Five groups of rabbits are used for this study. The administration route is intraarterial or intratumoral injection. The rabbits receive polysaccharide/cisplatin with or without a cross linker, such as calcium chloride.

Toxicity is assessed by measuring BUN, SGOT/SGPT, electrolyte level, cell counts, platelet and creatinine level after administration of polysaccharide/anticancer agents or polyamino acids/isotope chelation.

Example 5

Non-Cancer Embodiments of the Present Invention

The methods of the present invention are useful for any application of a therapeutic agent to a specific location in the body of an individual, such as when administration of a therapeutic agent systemically is undesirable. For instance, treatment of endometriosis with the methods of the present invention, preferably under laproscopic guidance, circumvents the undesirable side effects produced by systemic administration of hormone. Alternatively, an abscess, boil, inflammation, or infection may be treated locally with antibiotics without administering elevated levels of the antibiotic orally, with the intention of only treating the site in question. Also, bone degeneration, such as in a disc of the spine, may be treated by applying bone morpogenetic proteins to the site of the bone defect.

Example 6

Hydrogel Release Testing

Figure 4:
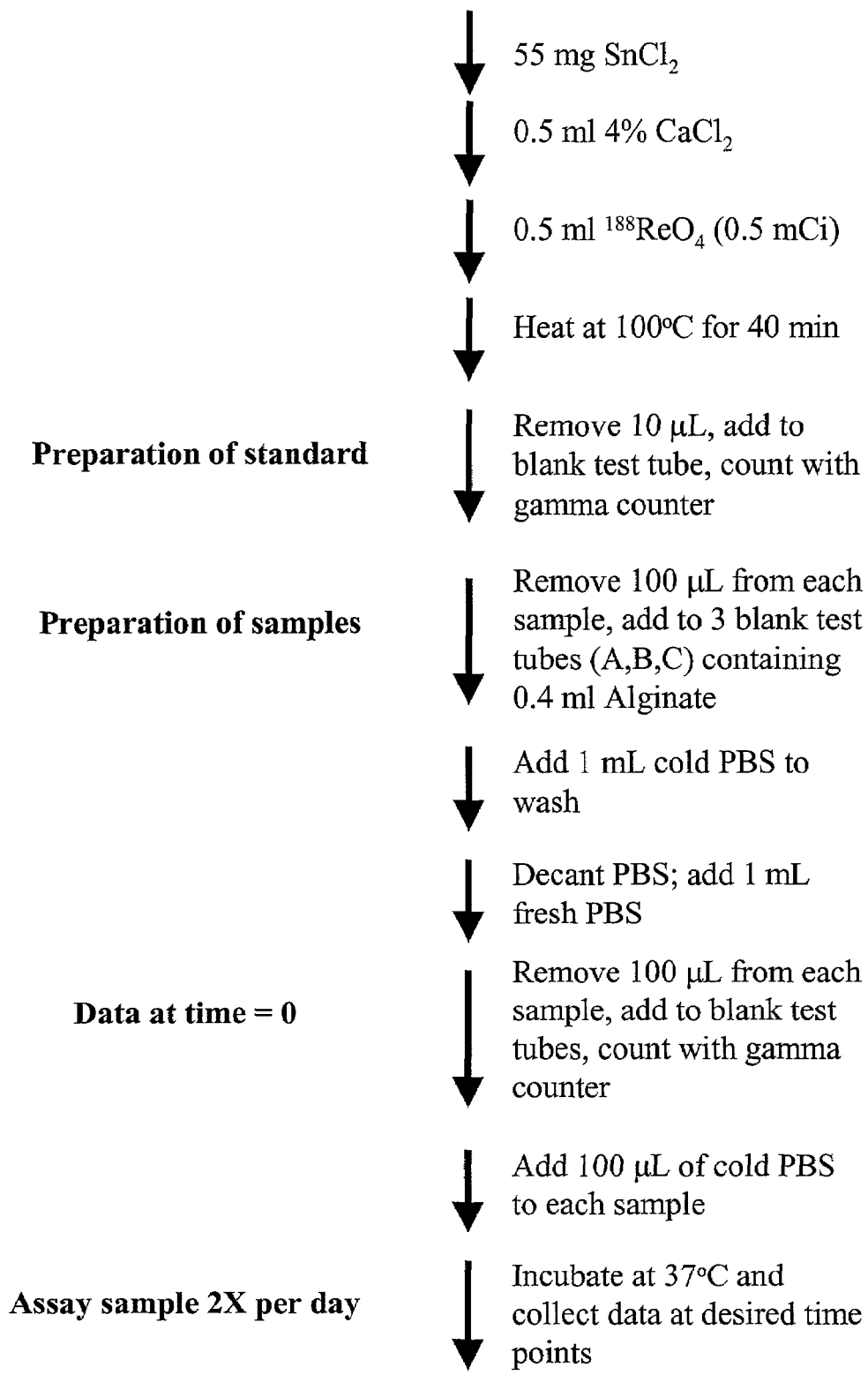
FIG. 4 illustrates one embodiment for preparation of $^{188}$Rhenium-hydragel.

FIG. 4 illustrates one embodiment directed to the preparation of a hydrogel comprising a radionuclide.

Table 5 demonstrates that significantly low percentages of radionuclide are released from the hydrogel. Generally, fifty mg of tin chloride (II) was dissolved in 0.2 mL of water and labeled with Re-188 (from W-188). The hydrogel was formed by adding alginate and calcium chloride.

TABLE 5

RELEASE OF RADIONUCLIDE

| STANDARD | DATE | TIME | COUNTS/0.01 cc | COUNTS/0.1 cc |
|---|---|---|---|---|
| | 01-Oct. | 1730 | 361611 | 3616110 |

| COUNT # | DATE | TIME | TOTAL ACT (uCi) | COUNTS/0.1 cc | % of DOSE RELEASED | ACCUMULATED % RELEASE |
|---|---|---|---|---|---|---|
| VIAL A ||||||| 
| 0 | 01-Oct. | 0 | 40.5 | 1829.37 | 0.05 | 0.05 |
| 1 | 02-Oct. | 16 | 21.4 | 23933.10 | 0.66 | 0.71 |
| 2 | 02-Oct. | 24 | 15.2 | 24074.00 | 0.67 | 1.38 |
| 3 | 03-Oct. | 40.5 | 7.8 | 21640.30 | 0.60 | 1.98 |
| 4 | 03-Oct. | 47.5 | 5.6 | 26815.70 | 0.74 | 2.72 |
| 5 | 04-Oct. | 63.5 | 3.3 | 26796.30 | 0.74 | 3.46 |
| 6 | 04-Oct. | 70.5 | 2.3 | 26042.70 | 0.72 | 4.18 |
| 7 | 05-Oct. | 91.5 | 1.3 | 20746.70 | 0.57 | 4.75 |
| 8 | 05-Oct. | 95.5 | — | 23502.20 | 0.65 | 5.40 |
| 9 | 06-Oct. | 115.5 | — | 11712.40 | 0.32 | 5.73 |
| | | | | | 5.73 | |
| VIAL B ||||||| 
| 0 | 01-Oct. | 0 | 40.7 | 3320.88 | 0.09 | 0.09 |
| 1 | 02-Oct. | 16 | 21 | 28206.50 | 0.78 | 0.87 |
| 2 | 02-Oct. | 24 | 15.2 | 22032.70 | 0.61 | 1.48 |
| 3 | 03-Oct. | 40.5 | 8 | 23000.00 | 0.64 | 2.12 |
| 4 | 03-Oct. | 47.5 | 6 | 30530.30 | 0.84 | 2.96 |
| 5 | 04-Oct. | 63.5 | 3.2 | 28015.70 | 0.77 | 3.74 |
| 6 | 04-Oct. | 70.5 | 2.3 | 22574.00 | 0.62 | 4.36 |
| 7 | 05-Oct. | 91.5 | 1.1 | 18444.70 | 0.51 | 4.87 |
| 8 | 05-Oct. | 95.5 | — | 20218.00 | 0.56 | 5.43 |
| 9 | 06-Oct. | 115.5 | — | 11807.30 | 0.33 | 5.76 |
| | | | | | 5.76 | |
| VIAL C ||||||| 
| 0 | 01-Oct. | 0 | 42.4 | 4955.99 | 0.14 | 0.14 |
| 1 | 02-Oct. | 16 | 21.9 | 23585.40 | 0.65 | 0.79 |
| 2 | 02-Oct. | 24 | 15.7 | 25570.40 | 0.71 | 1.50 |
| 3 | 03-Oct. | 40.5 | 8.1 | 24233.00 | 0.67 | 2.17 |
| 4 | 03-Oct. | 47.5 | 5.8 | 31738.00 | 0.88 | 3.04 |
| 5 | 04-Oct. | 63.5 | 3.1 | 28961.10 | 0.80 | 3.85 |
| 6 | 04-Oct. | 70.5 | 2.3 | 27377.10 | 0.76 | 4.60 |
| 7 | 05-Oct. | 91.5 | 1.2 | 19128.10 | 0.53 | 5.13 |
| 8 | 05-Oct. | 95.5 | — | 25308.90 | 0.70 | 5.83 |
| 9 | 06-Oct. | 115.5 | — | 13458.60 | 0.37 | 6.20 |
| | | | | | 6.20 | |

SUMMARY

| COUNT # | DATE | TIME | COUNTS/ 0.1 cc A | COUNTS/ 0.1 cc B | COUNTS/ 0.1 cc C | AVG CTS | % of DOSE RELEASED | ACCUMULATED % RELEASE |
|---|---|---|---|---|---|---|---|---|
| 0 | 01-Oct. | 0 | 1829.37 | 3320.88 | 4955.99 | 3368.75 | 0.09 | 0.09 |
| 1 | 02-Oct. | 16 | 23933.10 | 28206.50 | 23585.40 | 25241.67 | 0.70 | 0.79 |
| 2 | 02-Oct. | 24 | 24074.00 | 22032.70 | 25570.40 | 23892.37 | 0.66 | 1.45 |
| 3 | 03-Oct. | 40.5 | 21640.30 | 23000.00 | 24233.00 | 22957.77 | 0.63 | 2.09 |
| 4 | 03-Oct. | 47.5 | 26815.70 | 30530.30 | 31738.00 | 29694.67 | 0.82 | 2.91 |
| 5 | 04-Oct. | 63.5 | 26796.30 | 28015.70 | 28961.10 | 27924.37 | 0.77 | 3.68 |
| 6 | 04-Oct. | 70.5 | 26042.70 | 22574.00 | 27377.10 | 25331.27 | 0.70 | 4.38 |
| 7 | 05-Oct. | 91.5 | 20746.70 | 18444.70 | 19128.10 | 19439.83 | 0.54 | 4.92 |
| 8 | 05-Oct. | 95.5 | 23502.20 | 20218.00 | 25308.90 | 23009.70 | 0.64 | 5.55 |
| 9 | 06-Oct. | 115.5 | 11712.40 | 11807.30 | 13458.60 | 12326.10 | 0.34 | 5.90 |
| | | | | | | | 5.90 | |

Figure 5:
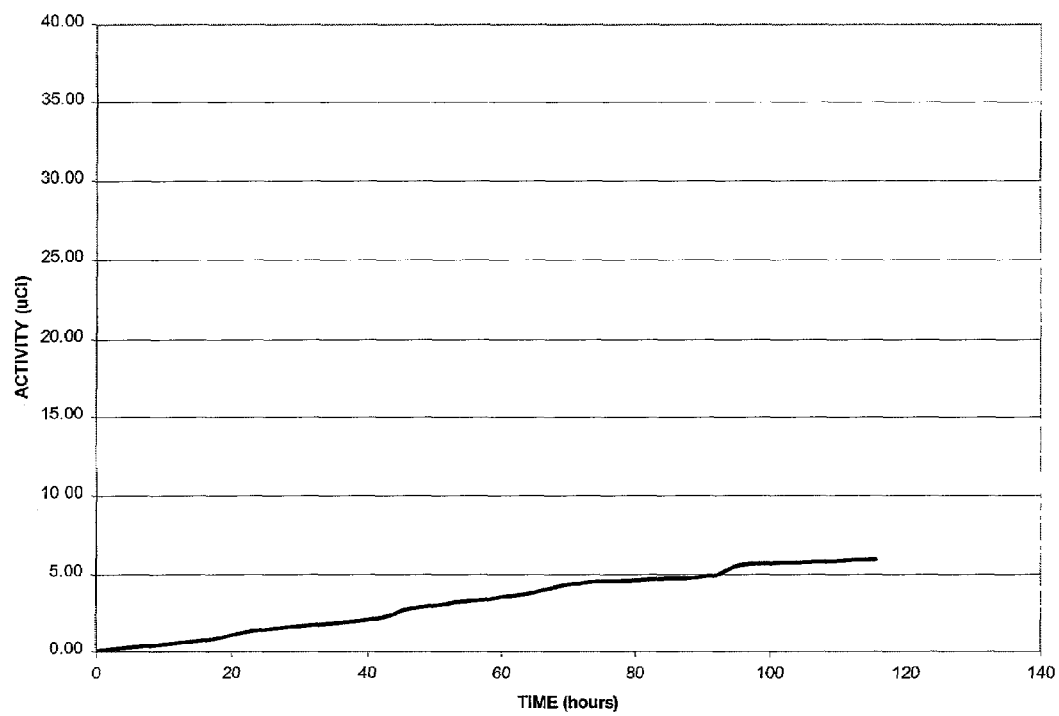
FIG. 5 illustrates accumulated rhenium-188 release by hydragel.
Figure 6:
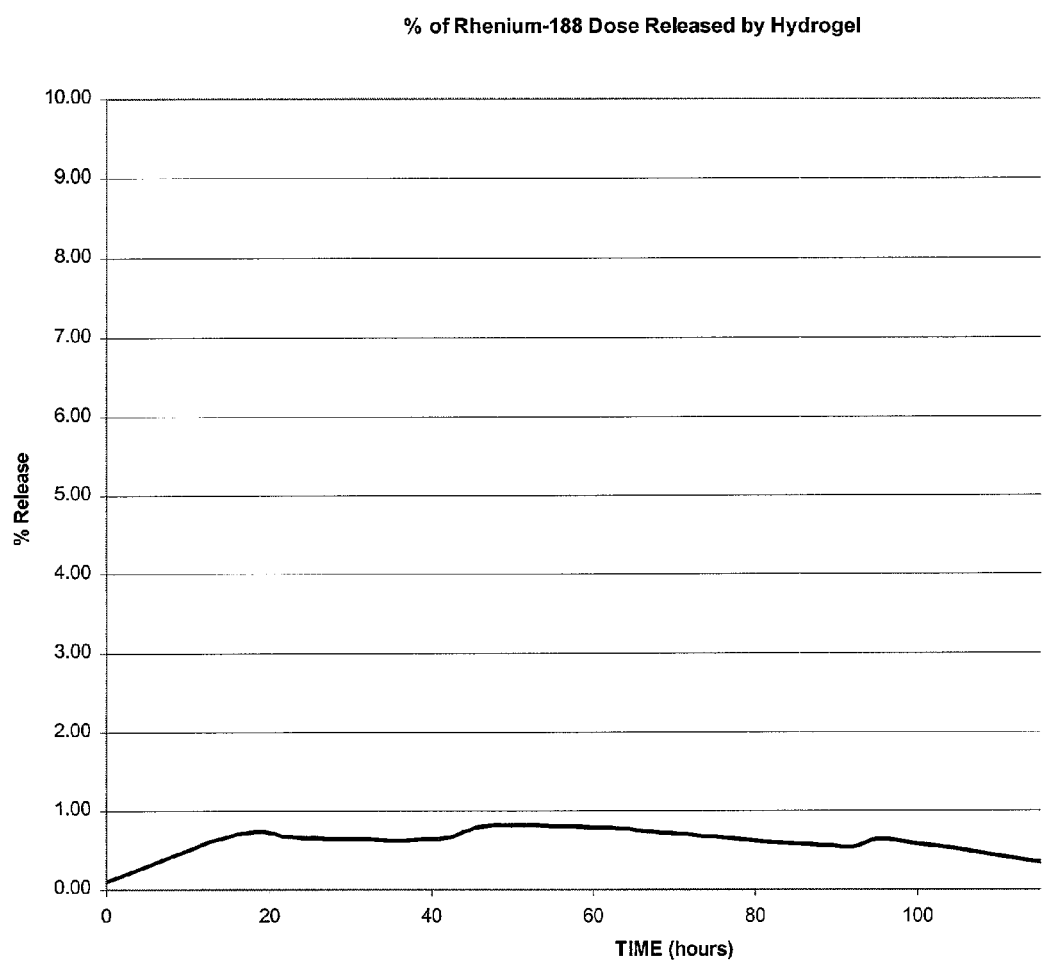
FIG. 6 demonstrates % of rhenium-188 dose released by hydragel.

Table 6 shows an experiment wherein similar methods were utilized to generate and test the hydrogel release of radionuclide. The data is illustrated in FIGS. 5 and 6. FIG. 5 shows activity released over time, whereas FIG. 6 shows % release over time.

TABLE 6

TOTAL AND PERCENTAGE OF DOSE RADIONUCLIDE RELEASE

| TIME | TOTAL RELEASE |
|---|---|
| 0 | 0.09 |
| 16 | 0.79 |
| 24 | 1.45 |
| 40.5 | 2.09 |
| 47.5 | 2.91 |
| 63.5 | 3.68 |
| 70.5 | 4.38 |
| 91.5 | 4.92 |
| 95.5 | 5.55 |
| 115.5 | 5.90 |

| TIME | % of DOSE RELEASED |
|---|---|
| 0 | 0.09 |
| 16 | 0.70 |
| 24 | 0.66 |
| 40.5 | 0.63 |
| 47.5 | 0.82 |
| 63.5 | 0.77 |
| 70.5 | 0.70 |
| 91.5 | 0.54 |
| 95.5 | 0.64 |
| 115.5 | 0.34 |

Example 7

In Vivo Antitumor Potency

Female Fischer 344 rats (150±25 g) (Harlan Sprague-Dawley; Indianapolis, Ind.) were inoculated subcutaneously with 0.1 ml of mammary tumor cells from the RBA CRL-1747 rat breast cancer cell line ($10^6$ cells/rat) into the hind legs. Studies were performed 14 to 17 days after implantation when tumors reached approximately 1 cm in diameter. Each animal was injected intratumorally with $^{188}$Re-tin (II) hydrogel or $^{188}$Re-(perrheneate) (0.5 mCi/rat, n=3 rats/group). In a specific embodiment, a device as shown in FIGS. 7 and 8 is utilized for the injection. $^{188}$ Re-tin (II) hydrogel was formulated as described in the in vitro release studies described in Example 6. Tumor volumes and body weight were recorded daily for sixty days. Tumor volumes were measured as [length (1)×width (w)×thickness (h)]/2. Loss of body weight of about 15% is considered a chemical-induced toxic effect. As illustrated in FIG. 9, the inventive $^{188}$Re-tin (II) hydrogel complex at a single injection is effective in vivo against cancer, such as breast cancer.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents

U.S. Pat. No. 4,608,251 issued Aug. 26, 1986.
U.S. Pat. No. 4,601,903 issued Jul. 22, 1986.
U.S. Pat. No. 4,599,231 issued Jul. 8, 1986.
U.S. Pat. No. 4,599,230 issued Jul. 8, 1986.
U.S. Pat. No. 4,596,792 issued Jun. 24, 1986.
U.S. Pat. No. 4,642,104 issued Feb. 10, 1987.
U.S. Pat. No. 4,879,236 issued Nov. 7, 1989.
U.S. Pat. No. 5,257,970 issued Nov. 2, 1993.
U.S. Pat. No. 5,928,906 issued Jul. 27, 1999.
U.S. Pat. No. 4,683,202 issued Jul. 28, 1987.
U.S. Pat. No. 5,871,986 issued Feb. 16, 1999.
U.S. Pat. No. 5,925,565 issued Jul. 20, 1999.
U.S. Pat. No. 5,935,819 filed Aug. 10, 1999.
Chinese Patent No. 1252310 issued May 10, 2000.
Japanese Patent No. 10236984 issued Sep. 8, 1998.
Japanese Patent No. 7097401 issued Apr. 11, 1995.
PCT publication number WO 00/00222 with an international application number PCT/US99/14206 and an international filing date of Jun. 25, 1999.
PCT publication number WO 00/38651 with an international application number PCT/US99/29401 and an international filing date of Dec. 10, 1999.

Publications

Almendro et al., "Cloning of the human platelet endothelial cell adhesion molecule-1 promoter and its tissue-specific expression. Structural and functional characterization," *J. Immunol.*, 157(12):5411–5421, 1996.
Arap et al., *Cancer Res.*, 55:1351–1354,1995.
Ausubel et al., 1994.
Bakhshi et al., 1985.
Banghiam A D, Standish M M, Miller N. (1965) Cation permeability of phospholipid model membranes: effect of narcotics. Nature. 1965 Dec. 25;208(17):1295–7.
Burris, H. A., Vogel, C. L., Castro, D., Mishra, L., Schwarz, M., Spencer, S., Oakes, D. D., Korey, A., Orenberg, E. K. (1998) Intratumoral cisplatin/epinephrine-injectable gel as a palliative treatment for accessible solid tumors: a multicenter pilot study. Otolaryngology-Head and Neck Surgery 118(4): 496–503.
Caldas et al., *Nat. Genet.*, 8:27–32,1994.
Carbonelli et al. "A plasmid vector for isolation of strong promoters in *E. coli*," FEMS *Microbiol Lett.* 177(1): 75–82, 1999.
Chandler et al., "RNA splicing specificity determined by the coordinated action of RNA recognition motifs in SR proteins," *Proc Natl Acad Sci USA.* 94(8):3596–3601, 1997.
Cheng et al, *Cancer Res.*, 54:5547–5551,1994.
Cleary and Sklar, 1985.
Cleary et al., 1986.
Cocea, "Duplication of a region in the multiple cloning site of a plasmid vector to enhance cloning-mediated addition of restriction sites to a DNA fragment," *Biotechniques,* 23:814–816, 1997.
Deamer and Uster, "Liposome Preparation: Methods and Mechanisms," LIPOSOMES, M. Ostro ed. (1983).
Downs, E. C., Robertson, N. E., Riss, T. L., Plunkett, M. L. Calcium alginate beads as a slow-release system for delivering angiogenic molecules in vivo and in vitro. J. Cellul. Physiol. 152:422–429.
Everett et al. (1953).
Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87–104, 1991.
Gregoriadis, DRUG CARRIERS IN BIOLOGY AND MEDICINE, G. Gregoriadis (ed.), 1979, pp. 287–341.

Harbord MG, Singh R, Morony S. (1999) SPECT abnormalities in Landau-Kleffner syndrome. J Clin Neurosci. 1999 January;6(1):9–16.

Hollstein et al., Science, 253:49–53, 1991.

Hussussian et al., *Nature Genetics,* 15–21, 1994.

Jackson, J. K., Gleave, M. E., Yago, V., Beraldi, E., Hunter, W. L., Burt, H. M. (2000) The suppression of human prostate tumor growth in mice by the intratumoral injection of a slow-release polymeric paste formulation of paclitaxel. Cancer Res. 60:4146–4151.

Kamb et al., Nature Genetics, 8:22–26,1994a.

Kamb et al., Science, 2674:436–440,1994b.

Kaneda et al., "Increased expression of DNA cointroduced with nuclear protein in adult rat liver," *Science,* 243: 375–378, 1989.

Kato et al., "Expression of hepatitis B virus surface antigen in adult rat liver," *J. Biol. Chem.,* 266:3361–3364, 1991.

Kerr et al., 1972.

Kitizawa, H., Sato, H., Adachi, I., Masuko, Y., Horikoshi, I. (1997) Microdialysis assessment of fibrin glue containing sodium alginate for local delivery of doxorubicin in tumor-bearing rats. Biol. Pharm. Bull. 20(3): 278–281.

Kraus et al., "Alternative promoter usage and tissue specific expression of the mouse somatostatin receptor 2 gene," FEBS Lett., 428(3):165–170, 1998.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," *J Biol. Chem.,* 274(12):8282–8290, 1999.

Lee et al., "Activation of beta3-adrenoceptors by exogenous dopamine to lower glucose uptake into rat adipocytes," *J Auton Nerv Syst.* 74(2–3):86–90, 1997.

Levenson et al., "Internal ribosomal entry site-containing retroviral vectors with green fluorescent protein and drug resistance markers," *Human Gene Therapy,* 9:1233–1236, 1998.

Macejak and Sarnow, "Internal initiation of translation mediated by the 5' leader of a cellular mRNA," Nature, 353(6339):90–94, 1990.

Maniatis et al., 1988.

Miller, B. H., Shavin, J. S., Cognetta, A., Taylor, J. R., Salasche, S., Korey, A., Orenberg, E. K. (1997) Nonsurgical treatment of basal cell carcinomas with intralesional 5-fluorouracil/epinephrine injectable gel. J. Amer. Acad. Derm. 36(1): 72–77.

Monga, S. P. S., Wadleigh, R., Sharma, A., Adib, H., Strader, D., Singh, G., Harmon, J. W., Berlin, M., Monga, D. K., Mishra, L. (2000) Intratumoral therapy of cisplatin/epinephrine injectable gel for palliation in patients with obstructive esophageal cancer. Am.J. Clin. Oncol. 23(4): 386–392.

Mori et al., 1994.

Nicolau et al., "Liposomes as carriers for in vivo gene transfer and expression," *Methods Enzymol.,* 149:157–176, 1987.

Ning, S., Yu, N., Brown, D. M., Kanekal, S., Knox, S. J. (1999) Radiosensitization by intratumoral administration of cisplatin in a sustained-release drug delivery system. Radiother. and Oncol. 50:215–223.

Nobri et al, *Nature,* 368:753–756,1995.

Okamoto et al., Proc. Natl. Acad. Sci. USA, 91:11045–11049,1994.

Orlow et al., 1994.

Pelletier and Sonenberg, "Internal initiation of translation of eukaryotic mRNA directed by a sequence derived from poliovirus RNA," *Nature,* 334:320–325, 1988.

"Remington's Pharmaceutical Sciences" 15 th Edition, pages 1035–1038, 1570–1580.

Serrano et al., *Nature,* 366:704–707,1993.

Serrano et al., *Science,* 267:249–252,1995.

Smith, J. P., Kanekal, S., Parawaran, M. B., Chen, J. Y., Jones, R. E., Orenberg, E. K., Yu, N. Y. (1999) Drug retention and distribution after intratumoral chemotherapy with fluorouracil/epinephrine injectable gel in human pancreatic cancer xenografts. Cancer Chemother. Pharmacol. 44: 267–274.

Smith and Rutledge, "Chemotherapy in advanced ovarian cancer," *Natl. Cancer Inst. Monogr.,* 42:141–143, 1975.

Szoka and Papahadjopoulos, *Proc. Nat'l Acad. Sci. U S.A.* 75:4194–98 (1978).

Tsujimoto et al., 1985.

Tsujimoto and Croce, 1986.

Tsumaki et al., "Modular arrangement of cartilage- and neural tissue-specific cis-elements in the mouse alpha2 (XI) collagen promoter," *J Biol. Chem.* 273(36):22861–22864, 1998.

Weinberg, *Science,* 254:1138–1146, 1991.

Wong et al., "Appearance of β-lactamase activity in animal cells upon liposome mediated gene transfer," *Gene,* 10:87–94, 1980.

Wu et al., 1997

Young et al., *N Engl J Med.* 7;299(23):1261–1266, 1978.

Zhao-Emonet et al., 1998.

One skilled in the art readily appreciates that the present invention is well adapted to carry out the objectives and obtain the ends and advantages mentioned as well as those inherent therein. Methods, procedures, techniques and kits described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method of dispensing a therapeutic agent in situ to a localized region in an individual comprising administering to said region a polymer composition that comprises a biocompatible polymer, a cross-linking composition that comprises a cross-linker, and the therapeutic agent, wherein the biocompatible polymer and the cross-linking composition are administered to allow formation of a cross-linked polymer in situ at the localized region, which cross-linked polymer comprises the therapeutic agent, and wherein the biocompatible polymer and the cross-linking composition are administered to the localized region from separate containers, wherein a first container comprises the biocompatible polymer and a second container comprises the cross-linking composition.

2. The method of claim 1, wherein the biocompatible polymer comprises the therapeutic agent.

3. The method of claim 1, wherein the polymer composition and the cross-linking composition are separately administered to the localized region.

4. The method of claim 1, wherein the first and second containers are syringes.

5. The method of claim 3, wherein the separate administrations of said polymer composition and said cross-linking composition are by syringe.

6. The method of claim 1, wherein the polymer composition and cross-linking compositions are administered separately from a syringe having at least two compartments, said compartments further defined as said separate containers.

7. The method of claim 1, wherein the polymer is a polysaccharide, a polyamino acid polymer, or a combination thereof.

8. The method of claim 7, wherein the polymer is a polysaccharide, and the polysaccharide polymer is an alginate, hydroxycellulose, chondroitin, chitosan, hyaluronate, dextran, or starch.

9. The method of claim 7, wherein the polymer is a polyamino acid, and the polyamino acid is a polyglutamate or a polyaspartate.

10. The method of claim 1, wherein said cross-linking agent is a salt of a divalent cation.

11. The method of claim 10, wherein said divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, $Sn^{2+}$, or $Be^{2+}$.

12. The method of claim 10, wherein said salt of a divalent cation is tin chloride, calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide.

13. The method of claim 1, wherein the therapeutic agent is a drug, a hormone, a gene therapy composition, a radionuclide, a nutriceutical, or a combination thereof.

14. The method of claim 13, wherein the therapeutic agent is a drug, and the drug is cisplatin, doxorubicin, Taxol, daunorubicin, mitomycin, actinomycin D, bleomycin, VP16, tumor necrosis factor, vincristine, vinblastine, carmustine, melphalan, cyclophosphamide, chlorambucil, bisulfan, lomustine, penicillin, erythromycin, amoxicillin, cefazolin, imipenem, aztreonam, sulbactam, linezolid, gentamicin, sulfamethoxazole, vancomycin, ciprofloxacin, fusidic acid, trimethoprim, metronidazole, clindamycin, mupirocin, amphotericin B, rifampin, fluconazoleor, or a combination thereof.

15. The method of claim 13, wherein the therapeutic agent is a hormone, and the hormone is luteinizing hormone, growth hormone, growth hormone releasing hormone, estrogen, progesterone, testosterone, androgen, corticotropin, prolactin, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetylcholine, aldosterone, angiotensin II, arginine vasopressin, bombesin, bradykinin, caerulein, calcitonin, cholecystokinin, chymodenin, corticosterone, cortisol, cortisone, dihydrotestosterone, dopamine, β-endorphin, epidermal growth factor, erthropoetin, estrdiol, fibroblast growth factor, gamma aminobutyric acid, gastric inhibitory peptide, gastrin, glucagon, histamine, human chorionic gonadotropin, human placental lactogen, inhibin, insulinlike growth factor I, insulinlike growth factor II, leucine enkaephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platlet-derived growth factor, prolactin inhibiting factor, prostacyclin I2, prostaglandin E2, prostaglandin F2a, relaxin, serotonin, serum thymic factor, substance P, thromboxane A2, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin D3, or a combination thereof.

16. The method of claim 13, wherein the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras ; myc, raf, erb, src, fms, jun, trk, ret, gsp, hst, bcl abl; Rb, CFTR, p16, p21, p27, p57, p73, C-CAM, APC, CTS-1, zac1, scFV ras, DCC, NF-1, NF- 2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF, G-CSF, or a combination thereof.

17. The method of claim 16, wherein the vector is a plasmid, an adenoviral vector, an adeno-associated viral vector, a retroviral vector, a liposome, or a combination thereof.

18. The method of claim of 13, wherein the therapeutic agent is a radionuclide, and the radionuclide is $^{188}Re$, $^{213}Bi$, $^{166}Ho$, $^{211}At$, or a combination thereof.

19. The method of claim 13, wherein the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelam, butcher's broom, calcium hydroxyl apatite, cascara sagrada, cat's claw, cetyl myristoleate, chamomile, chitosan, chlorella, chondroitin sulfate, chromium yeast, citrus aurantiurn, citrus seed extract, coenzyme Q10, colostrum, cordyceps, cranberry, creatine monohydrate, devil's claw, DHEA, DMG, dong quai, echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorbiza, potassium glycero phosphate, pygeum, quercetin, reishi, saw palmetto, schisandra, sea cucumber, selenium yeast bound, shark cartilage, shark liver oil, shiitake, shilajit, sodium copper chiorophyllin, spirulina, squalene, St. John's Wort, stevia, suma, tribulus (Bulgarian) triphala, tumeric, uva ursi, valerian, wild yam extract, willow bark, yohimbe bark extract, or a combination thereof.

20. A method of treating a tumor in situ in an individual comprising the steps of administering to said tumor a polymer composition that comprises a biocompatible polymer, a cross-linking composition that comprises a cross-linker, and a therapeutic agent, wherein the biocompatible polymer and the cross-linking composition are administered to allow formation of a cross-linked polymer in situ at the tumor, which cross linked polymer comprises the therapeutic agent, and wherein the biocompatible polymer and the cross-linking composition are administered to the tumor from separate containers, wherein a first container comprises the biocompatible polymer and a second container 21. The method of claim 20, wherein the biocompatible polymer comprises the therapeutic agent.

22. The method of claim 20, wherein the polymer composition and the cross-linking composition are separately administered to the localized region.

23. The method of claim 20, wherein the first and second containers are syringes.

24. The method of claim 22, wherein the separate administrations of said polymer composition and said cross-linking composition are by syringe.

25. The method of claim 20, wherein the polymer composition and cross-linking compositions are administered separately from a syringe having at least two compartments, said compartments further defined as said separate containers.

26. The method of claim 20, wherein the polymer is a polysaccharide, a polyamino acid polymer, or a combination thereof.

27. The method of claim 26, wherein the polymer is a polysaccharide, and the polysaccharide polymer is an alginate, hydroxycellulose, chondroitin, chitosan, hyaluronate, dextran or starch.

28. The method of claim 26, wherein the polymer is a polyainino acid, and the polyamino acid is a polyglutamate or a polyaspartate.

29. The method of claim 20, wherein said cross-linking agent is a salt of a divalent cation.

30. The method of claim 29, wherein said divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or Be2+.

31. The method of claim 29, wherein said salt of a divalent cation is tin chloride, calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide.

32. The method of claim 20, wherein said therapeutic agent is a drug, a hormone, a gene therapy composition, a radionuclide, a nutriceutical, or a combination thereof.

33. The method of claim 32, wherein the therapeutic agent is a drug, and the drug is cisplatin, doxorubicin, Taxol, daunorubicin, mitomycin, actinomycin D, bleomycin, VP16, tumor necrosis factor, vincristine, vinbiastine, carmustine, meiphalan, cyclophosphamide, chiorambucil, bisulfan, lomustine, penicillin, erythromycin, amoxicillin, cefazolin, imipenem, azireonani, sulbactam, linezolid, gentamicin, sulfaniethoxazole, vancomycin, ciprofloxacin, fusidic acid, trimethoprim, metronidazole, clindaniycin, mupirocin, amphotericin B, rifampin, fluconazoleor, or a combination thereof.

34. The method of claim 32, wherein the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epinephrine, norepinephrine, follicle stimulating hormone, insulin, acetyicholine, aldosterone, angiotensin II, arginine vasopressin, bombesin, bradykinin, caerulein, calcitonin, cholecystokinin, chymodemn, corticosterone, cortisol, cortisone, dihydrotestosterone, dopamine, β-endorphin, epidermal growth factor, erythropoietin, estradiol, fibroblast growth factor, gamma aminobutyric acid, gastric inhibitory peptide, gastrin, glucagon, histamine, human choriomc gonadotropin, human placental lactogen, inhibin, insulinlike growth factor I, insulinlike growth factor II, leucine enkephalin, leukotrienes, lysine vasopressin, lysyibradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin I2, prostaglandin E2, prostaglandin F2a, relaxin, serotonin, serum thymic factor, substance P. thromboxane A2, thymopoietin, thymosina, thyrotopin (thyroid stimulating hormone; TSH), thyrotropin releasing hormone, thyroxine, triiodothyronine, urogastrone, vasoactive intestinal peptide, vasotocin, vitamin D3, or a combination thereof.

35. The method of claim 32, wherein the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras ; myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF, G-CSF, or a combination thereof.

36. The method of claim 35, wherein the vector is a plasmid, an adenoviral vector, an adeno-associated viral vector, a retroviral vector, a liposome, or a combination thereof.

37. The method of claim 32, wherein the therapeutic agent is a radionuclide, and the radionuclide is $^{188}Re$, $^{213}Bi$, $^{166}Ho$, $^{211}At$, or a combination thereof.

38. The method of claim 32, wherein the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chiorella, chondroitin sulfate, chromium yeast, citrus aurantium, citrus seed extract, co-enzyme QIO, colostrum, cordyceps, cranberry, creatine monohydrate, devil's claw, DHEA, DMG, dong quai, echinacea, elderberry, ephedra, evening primrose oil, fever-few, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnema, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocinium sanctum, octacosonol, olivir, passion flower, pay d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, vohimbe bark extract, or a combination thereof.

39. A method of occluding an artery associated with a tumor in an individual comprising the step of administering to said tumor a polymer composition that comprises a biocompatible polymer and a cross-linking composition that comprises a cross-linker, wherein the biocompatible polymer and the cross-linking composition are administered to allow formation of the cross-linked polymer in situ at the tumor, wherein the biocompatible polymer and the cross-linking composition are administered to the tumor from separate containers, wherein a first container comprises the biocompatible polymer and a second container comprises the cross-linking composition.

40. The method of claim 39, wherein the biocompatible polymer further comprises a therapeutic agent.

41. The method of claim 39, wherein the polymer composition and the cross-linking composition are separately administered to the tumor.

42. The method of claim 39, wherein the first and second containers are svrinaes.

43. The method of claim 41, wherein the separate administrations of said polymer composition and said cross-linking composition are by syringe.

44. The method of claim 39, wherein the polymer composition and cross-linking compositions are administered separately from a syringe having at least two compartments, said compartments further defined as said separate containers.

45. The method of claim 39, wherein the polymer is a polysaccharide, a polyamino acid polymer, or a combination thereof.

46. The method of claim 45, wherein the polymer is a polysaccharide, and the polysaccharide polymer is an alginate, hydroxycellulose, chondroitin, chitosan, hyaluronate, dextran or starch.

47. The method of claim 45, wherein the polymer is a polyamino acid, and the polyamino acid is a polyglutaxnate or a polyaspartate.

48. The method of claim 39, wherein said cross-linking agent is a salt of a divalent cation.

49. The method of claim 48, wherein said divalent cation is $Ca^{2+}$, $Mg^{2+}$, $Mn^{2+}$, $Cu^{2+}$, $Cr^{2+}$, $Sr^{2+}$, $Zn^{2+}$, $Ra^{2+}$, or $Be^{2+}$.

50. The method of claim 48, wherein said salt of a divalent cation is tin chloride, calcium chloride, calcium sulfate, calcium phosphate, calcium carbonate, calcium chlorate, calcium fluoride, calcium bromide, magnesium chloride, magnesium sulfate, magnesium phosphate, magnesium carbonate, magnesium chlorate, magnesium fluoride, magnesium bromide, manganese chloride, manganese sulfate, manganese phosphate, manganese carbonate, manganese chlorate, manganese fluoride, manganese bromide, copper chloride, copper sulfate, copper phosphate, copper carbonate, copper chlorate, copper fluoride, copper bromide, chromium chloride, chromium sulfate, chromium phosphate, chromium carbonate, chromium chlorate, chromium fluoride, chromium bromide, strontium chloride, strontium sulfate, strontium phosphate, strontium carbonate, strontium chlorate, strontium fluoride, strontium bromide, zinc chloride, zinc sulfate, zinc phosphate, zinc carbonate, zinc chlorate, zinc fluoride, zinc bromide, radium chloride, radium sulfate, radium phosphate, radium carbonate, radium chlorate, radium fluoride, radium bromide, beryllium chloride, beryllium sulfate, beryllium phosphate, beryllium carbonate, beryllium chlorate, beryllium fluoride, or beryllium bromide.

51. The method of claim 47, wherein said therapeutic agent is a drug, a hormone, a gene therapy composition, a radionuclide, a nutriceutical, or a combination thereof.

52. The method of claim 51, wherein the therapeutic agent is a drug, and the drug is cisplatin, doxorubicin, Taxol, daunorubicin, mitomycin, actinomycin D, bleomycin, VP 16, tumor necrosis factor, vincristine, vinblastine, carmustine, meiphalan, cyclophosphamide, chlorambucil, bisulfan, lomustine, penicillin, erythromycin, amoxicillin, erythromycin, cefazolin, imipenem, aztreonam, sulbactam, linezolid, gentamicin, sulfamethoxazole, vancomycin, ciprofloxacin, fusidic acid, trimethoprim, 53. The method of claim 51, wherein the therapeutic agent is a hormone, and the hormone is luteinizing hormone releasing hormone, growth hormone, growth hormone releasing hormone, estrogen, progesterone, testosterone, androgen, corticotropin, prolactin, gonadotropin, somatotropin, somatostatin, somatotropin releasing hormone, gonadotropin releasing hormone, corticotropin releasing hormone, prolactin releasing hormone, pro-opiomelanocortin, melanotropin, calcitonin, gastrin, secretin, aldosterone, epmephrine, norepinephrine, follicle stimulating hormone, insulin. acetyicholine, aldosterone, angiotensin II, arginine vasopressin. bombesin, bradykinin. caerulein, calcitonin, cholecystokinin, chymodenin, corticosterone, cortisol, cortisone, dihydrotestosterone, dopamine, β-endorphin, epidermal growth factor, erythropoietin, estradiol, fibroblast growth factor, gamma amuiobutyric acid, gastric inhibitory peptide, gastrin, glucagon, histamine, human chorionic gonadotropin, human placental lactogen, inhibin, insulinlike growth factor I, insulinlike growth factor II, leucine enkephalin, leukotrienes, lysine vasopressin, lysylbradykinin, melanin concentrating hormone, α-melanocyte stimulating hormone, mesotocin, methionin enkephalin, motilin, MSH release inhibiting factor, Mullerian regression factor, nerve growth factor, neurotensin, oxytocin, pancreatic polypeptide, parathormone, platelet-derived growth factor, prolactin inhibiting factor, prostacyclin I2, prostaglandin E2, prostaglandin F2a, relaxin, serotonin, serum thymic factor, substance P, thromboxane A2, thymopoietin. thymosina, thyrotopin (thyroid stimulating hormone; TSH), thyrotropin releasing hormone, thyroxine, triiodothyronine, urogastrone, vasoactive intestinal peptide, vasotocin, vitamin D3, or a combination thereof.

54. The method of claim 51, wherein the therapeutic agent is a gene therapy composition, and the gene therapy composition is a vector containing p53, thymidine kinase, cytosine deaminase, oxidoreductase, thymidine kinase thymidilate kinase, deoxycytidine kinase, ras; myc, raf, erb, src, fms, jun, trk, ret, gsp, hst, bcl abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF, G-CSF, or a combination thereof.

55. The method of claim 54, wherein the vector is a plasmid, an adenoviral vector, an adeno-associated viral vector, a retroviral vector, a liposome, and a combination thereof.

56. The method of claim 51, wherein the therapeutic agent is a radionuclide, and the radionuclide is $^{188}$Re, $^{213}$Bi, $^{166}$Ho, $^{211}$At, or a combination thereof.

57. The method of claim 51, wherein the therapeutic agent is a nutriceutical, and the nutriceutical is arabinogalactan, acerola cherry, agnus castus (vitex), amla, andrographis, artichoke (globe), ashwagandha, astragalus, bacopa, beta 1,3 glucans, beta sitosterol, bilberry, borage oil, boswellia, broccoli cruciferous, bromelain, butcher's broom, calcium hydroxyl apatite, cascara sagrada, cat's claw, cetyl myristoleate, chamomile, chitosan, chiorella, chondroitin sulfate, chromium yeast, citrus aurantium, citrus seed extract, coenzyme QIO, colostruni, cordyceps, cranberry, creatine monohydrate, devil's claw, DHEA, DMG, doug quai, echinacea, elderberry, ephedra, evening primrose oil, feverfew, fish marine lipids, fish oil concentrate powder, fish protein powder, flaxseed oil, garcinia HCA, garlic T.A.P., germanium Ge-132, ginger, ginkgo, ginseng-American, ginseng-Siberian, ginseng-Asian, glucosamine, goldenseal, gotu kola, grapeseed extract, green tea extract, guarana, gymnenia, hawthorne, hops, horse chestnut, horsetail, kava kava, kola nut, lecithin, licorice, lipoic acid, lycopene, medium chain tri-glycerides, melatonin, milk thistle, MSM, muira puama, nag, nettles, noni, ocimum sanctum, octacosonol, olivir, passion flower, pau d'arcophosphatidylserine, picrorhiza, potassium glycero phosphate, pygeum, quercetin, reishi, saw palmetto, schisandra, sea cucumber, selenium yeast bound, shark cartilage, shark liver oil, shiitake, shilajit, sodium copper chlorophyllin, spirulina, squalene, St. John's Wort, stevia, suma, tribulus (Bulgarian) triphala, tumeric, uva ursi, valerian, wild yam extract, willow bark, yohimbe bark extract, or a combination thereof.

58. The method of claim 39, wherein said administration step occurs through a catheter.

59. A method of dispensing a therapeutic agent in situ to a localized region in an individual comprising administering to said region a polymer composition that comprises a biocompatible polymer, a cross-linking composition that comprises a cross-linker, and the therapeutic agent, wherein the polymer composition and the cross-linking composition are administered to allow formation of a cross-linked polymer in situ at the localized region, which cross-linked polymer comprises the therapeutic agent, wherein the polymer composition and the cross-linking composition are separately administered to the localized region by means of a single container having at least two compartments, wherein one compartment comprises the polymer composition and another compartment comprises the cross-linking composition.

60. A method of dispensing a therapeutic agent in situ to a localized region in an individual comprising administering to said region a polymer composition that comprises a biocompatible polymer, a cross-linking composition that comprises a cross-linker, and the therapeutic agent, wherein the polymer composition and the cross-linking composition are administered to allow formation of a cross-linked polymer in situ at the localized region, which cross-linked polymer comprises the therapeutic agent, wherein the polymer composition and the cross-linking composition are separately administered to the localized region by means of a single container having a hollow cylindrical compartment, wherein the polymer composition and cross-linking composition are administered separately through said compartment.

61. The method of claim 1, wherein said administration is to a tumor.

* * * * *

UNITED STATES PATENT AND TRADEMARK OFFICE
CERTIFICATE OF CORRECTION

PATENT NO. : 7,008,633 B2
APPLICATION NO. : 10/024678
DATED : March 7, 2006
INVENTOR(S) : David J. Yang et al.

It is certified that error appears in the above-identified patent and that said Letters Patent is hereby corrected as shown below:

Title page, left column, under [75] Inventors: . . . Ali Azhdarinia, Houston, TX (US) should be on the same line.
Title page, left column, under [75] Inventors: . . . E. Edmund Kim, Houston, TX (US) should be on the same line.
In Col. 67, line 56, after the third occurrence of "hormone" insert -- releasing hormone --.
In Col. 67, line 59, after "gonadotropin" insert -- , somatotropin, somatostatin, somatotropin releasing hormone, gonadotropin --.
In Col. 67, line 67, "erthropoetin" should read -- erythropoietin --.
In Col. 68, line 1, "estrdiol" should read -- estradiol --.
In Col. 68, line 5, "enkaephalin" should read -- enkephalin --.
In Col. 68, line 10, "platlet-derived" should read -- platelet-derived --.
In Col. 68, lines 22-23, "*ras* ; *myc, raf, erb, src, fms, jun, trk, ret, gsp, hst, bcl abl*," apply Italic font.
In Col. 68, line 24, "ras" apply Italic font.
In Col. 68, line 33, after the occurrence of "claim" delete "of".
In Col. 68, line 41, "bromelam" should read -- bromelain --.
In Col. 68, line 44, "aurantiurn" should read -- aurantium --.
In Col. 68, line 58, "picrorbiza" should read -- picrorhiza --.
In Col. 68, line 61, "chiorophyllin" should read -- chlorophyllin --.
In Col. 68, line 66, "in situ" apply Italic font.
In Col. 68, line 5, "in situ" apply Italic font.
In Col. 69, line 6, "cross linked" should read -- cross-linked --.
In Col. 69, line 10, after the "container" insert -- cthe cross-linking composition. --.
In Col. 69, line 34, "polyainino" should read -- polyamino --.
In Col. 70, line 2, "vinbiastine" should read -- vinblastine --.
In Col. 70, line 3, "meiphalan" should read -- melphalan --.
In Col. 70, line 20, "acetyicholine" should read -- acetylcholine --.
In Col. 70, line 22, "chymodemn" should read -- chymodenin --.
In Col. 70, line 26, "choriomc" should read -- chorionic --.
In Col. 70, line 29, "lysyibradykinin" should read -- lysylbradykinin --.
In Col. 70, line 37, "P." should read -- P, --.
In Col. 70, line 46-47, "*ras* ; *myc, raf, erb, src, fms, jun, trk, ret, gsp, hst, bcl abl, Rb*," apply Italic font.
In Col. 70, line 67, "chiorella" should read -- chlorella --.
In Col. 71, line 2, "QIO" should read -- Q10 --.
In Col. 71, line 13, "ocinium" should read -- ocimum --.
In Col. 71, line 14, "pay" should read -- pau --.

UNITED STATES PATENT AND TRADEMARK OFFICE
CERTIFICATE OF CORRECTION

PATENT NO. : 7,008,633 B2
APPLICATION NO. : 10/024678
DATED : March 7, 2006
INVENTOR(S) : David J. Yang et al.

It is certified that error appears in the above-identified patent and that said Letters Patent is hereby corrected as shown below:

In Col. 71, line 21, "vohimbe" should read -- yohimbe --.
In Col. 71, line 41, "svrinaes" should read -- syringes --.
In Col. 71, line 58, "polyglutaxnate" should read -- polyglutamate --.
In Col. 71, line 63, "$Ra.^{2+}$, or $Be^{2+}$." should read -- $Ra^{2+}$, $Sn^{2+}$, or $Be^{2+}$. --.
In Col. 72, line 27, "meiphalan" should read -- melphalan --.
In Col. 72, line 31, after the occurrence of "trimethoprim," insert -- metronidazole, clindamycin, mupirocin, amphotericin B, rifampin, fluconazoleor, or a combination thereof. --.
In Col. 72, line 41, "epmephrine" should read -- epinephrine --.
In Col. 72, line 42, "acetyicholine" should read -- acetylcholine --.
In Col. 72, line 43, "vasopressin." should read -- vasopressin, --.
In Col. 72, line 43, "bradykinin." should read -- bradykinin, --.
In Col. 72, line 47, "amuiobutyric" should read -- aminobutyric --.
In Col. 72, line 59, "thymopoietin." should read -- thymopoietin, --.
In Col. 73, line 2-3, "*ras ; myc, raf, erb, src, fms, jun, trk, ret, gsp, hst, bcl abl,*" apply Italic font.
In Col. 74, line 22, "in situ" apply Italic font.
In Col. 74, line 29, "in situ" apply Italic font.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,008,633 B2 | Page 1 of 2 |
| APPLICATION NO. | : 10/024678 | |
| DATED | : March 7, 2006 | |
| INVENTOR(S) | : David J. Yang et al. | |

It is certified that error appears in the above-identified patent and that said Letters Patent is hereby corrected as shown below:

Title page, left column, under [75] Inventors: . . . Ali Azhdarinia, Houston, TX (US) should be on the same line.
Title page, left column, under [75] Inventors: . . . E. Edmund Kim, Houston, TX (US) should be on the same line.
In Col. 67, line 56, after the third occurrence of "hormone" insert -- releasing hormone --.
In Col. 67, line 59, after "gonadotropin" insert -- , somatotropin, somatostatin, somatotropin releasing hormone, gonadotropin --.
In Col. 67, line 67, "erthropoetin" should read -- erythropoietin --.
In Col. 68, line 1, "estrdiol" should read -- estradiol --.
In Col. 68, line 5, "enkaephalin" should read -- enkephalin --.
In Col. 68, line 10, "platlet-derived" should read -- platelet-derived --.
In Col. 68, lines 22-23, "*ras* ; *myc, raf, erb, src, fms, jun, trk, ret, gsp, hst, bcl abl*," apply Italic font.
In Col. 68, line 24, "*ras*" apply Italic font.
In Col. 68, line 33, after the occurrence of "claim" delete "of".
In Col. 68, line 41, "bromelam" should read -- bromelain --.
In Col. 68, line 44, "aurantiurn" should read -- aurantium --.
In Col. 68, line 58, "picorbiza" should read -- picrorhiza --.
In Col. 68, line 61, "chiorophyllin" should read -- chlorophyllin --.
In Col. 68, line 66, "in situ" apply Italic font.
In Col. 68, line 5, "in situ" apply Italic font.
In Col. 69, line 6, "cross linked" should read -- cross-linked --.
In Col. 69, line 34, "polyainino" should read -- polyamino --.
In Col. 70, line 2, "vinbiastine" should read -- vinblastine --.
In Col. 70, line 3, "meiphalan" should read -- melphalan --.
In Col. 70, line 20, "acetyicholine" should read -- acetylcholine --.
In Col. 70, line 22, "chymodemn" should read -- chymodenin --.
In Col. 70, line 26, "choriomc" should read -- chorionic --.
In Col. 70, line 29, "lysyibradykinin" should read -- lysylbradykinin --.
In Col. 70, line 37, "P." should read -- P, --.
In Col. 70, line 46-47, "*ras* ; *myc, raf, erb, src, fms, jun, trk, ret, gsp, hst, bcl abl, Rb*," apply Italic font.
In Col. 70, line 67, "chiorella" should read -- chlorella --.
In Col. 71, line 2, "QIO" should read -- Q10 --.
In Col. 71, line 13, "ocinium" should read -- ocimum --.
In Col. 71, line 14, "pay" should read -- pau --.

UNITED STATES PATENT AND TRADEMARK OFFICE
CERTIFICATE OF CORRECTION

PATENT NO. : 7,008,633 B2
APPLICATION NO. : 10/024678
DATED : March 7, 2006
INVENTOR(S) : David J. Yang et al.

It is certified that error appears in the above-identified patent and that said Letters Patent is hereby corrected as shown below:

In Col. 71, line 21, "vohimbe" should read -- yohimbe --.
In Col. 71, line 41, "svrinaes" should read -- syringes --.
In Col. 71, line 58, "polyglutaxnate" should read -- polyglutamate --.
In Col. 71, line 63, "Ra.$^{2+}$, or Be $^{2+}$." should read -- Ra$^{2+}$, Sn$^{2+}$, or Be$^{2+}$. --.
In Col. 72, line 27, "meiphalan" should read -- melphalan --.
In Col. 72, line 31, after the occurrence of "trimethoprim," insert -- metronidazole, clindamycin, mupirocin, amphotericin B, rifampin, fluconazoleor, or a combination thereof. --.
In Col. 72, line 41, "epmephrine" should read -- epinephrine --.
In Col. 72, line 42, "acetyicholine" should read -- acetylcholine --.
In Col. 72, line 43, "vasopressin." should read -- vasopressin, --.
In Col. 72, line 43, "bradykinin." should read -- bradykinin, --.
In Col. 72, line 47, "amuiobutyric" should read -- aminobutyric --.
In Col. 72, line 59, "thymopoietin." should read -- thymopoietin, --.
In Col. 73, line 1-2, "*ras* ; *myc, raf, erb, src, fms, jun, trk, ret, gsp, hst, bcl abl*," apply Italic font.
In Col. 74, line 22, "in situ" apply Italic font.
In Col. 74, line 29, "in situ" apply Italic font.

This certificate supersedes the Certificate of Correction issued October 7, 2008.

Signed and Sealed this

Fourth Day of November, 2008

JON W. DUDAS
*Director of the United States Patent and Trademark Office*